(12) United States Patent
Hamachi et al.

(10) Patent No.: US 8,093,060 B2
(45) Date of Patent: Jan. 10, 2012

(54) MULTISITE PHOSPHORYLATED PEPTIDE (PROTEIN) RECOGNIZING COMPOUND AND DETECTION METHOD, IMAGING METHOD, ALZHEIMER'S DISEASE DIAGNOSING METHOD AND REAGENT KIT USING THE SAME

(75) Inventors: Itaru Hamachi, Kyoto (JP); Fumio Yamauchi, Yokohama (JP); Tetsuya Yano, Tsukuba (JP); Kimihiro Yoshimura, Yokohama (JP); Akio Ojida, Kyoto (JP); Takashi Sakamoto, Kyoto (JP); Masaaki Inoue, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 94 days.

(21) Appl. No.: 12/393,011

(22) Filed: Feb. 25, 2009

(65) Prior Publication Data
US 2009/0233373 A1     Sep. 17, 2009

(30) Foreign Application Priority Data

Feb. 28, 2008   (JP) .................................. 2008-048281

(51) Int. Cl.
*G01N 33/48* (2006.01)
(52) U.S. Cl. .......... 436/86; 436/103; 436/104; 436/164; 252/408.1; 546/12; 546/13; 546/264
(58) Field of Classification Search .............. 252/408.1; 546/12, 13, 264; 436/15, 86, 104, 103, 164
See application file for complete search history.

(56) References Cited

U.S. PATENT DOCUMENTS

| | | | |
|---|---|---|---|
| 5,236,694 A | 8/1993 | Antich et al. | |
| 5,665,597 A | 9/1997 | Imamura et al. | |
| 5,670,315 A | 9/1997 | Yamamoto et al. | |
| 5,679,568 A | 10/1997 | Imamura et al. | |
| 5,753,466 A | 5/1998 | Yano et al. | |
| 5,803,664 A | 9/1998 | Kawabata et al. | |
| 5,807,736 A | 9/1998 | Kozaki et al. | |
| 5,854,059 A | 12/1998 | Kozaki et al. | |
| 5,945,331 A | 8/1999 | Kozaki et al. | |
| 5,962,305 A | 10/1999 | Mihara et al. | |

(Continued)

FOREIGN PATENT DOCUMENTS

EP     0 592 306 A2    4/1994

(Continued)

OTHER PUBLICATIONS

Harriman, Anthony, et al. "Electron transfer in self-assembled orthogonal structures." Journal of Physical Chemistry A (2006) 110 p. 7994-8002.*

(Continued)

*Primary Examiner* — Yelena G Gakh
*Assistant Examiner* — Christopher A Hixson
(74) *Attorney, Agent, or Firm* — Fitzpatrick, Cella, Harper & Scinto

(57) ABSTRACT

A compound which captures a multisite phosphorylated peptide or protein specifically to a phosphorylation site and a method for detecting the peptide or protein using the compound. Particularly, a compound which specifically detects an excessively phosphorylated tau protein observed in the brain affected by Alzheimer's disease and a method for diagnosing Alzheimer's disease in vitro or in vivo using the compound are provided. By bringing a metal complex compound having two dipicolylamine (Dpa) moieties and a spacer including a chromogenic or luminescent functional or atom group into contact with a multisite phosphorylated peptide or protein, the compound recognizes the distance between phosphate groups and specifically binds to the peptide or protein, and a multisite phosphorylated peptide or protein or kinase activity is optically detected by measuring the change, or a multisite phosphorylated peptide or protein or kinase activity is imaged by an optical imaging method applying the change in luminescence.

6 Claims, 17 Drawing Sheets

1

U.S. PATENT DOCUMENTS

| | | | |
|---|---|---|---|
| 6,004,772 | A | 12/1999 | Imamura et al. |
| 6,017,746 | A | 1/2000 | Imamura et al. |
| 6,472,191 | B1 | 10/2002 | Yano et al. |
| 6,479,621 | B2 | 11/2002 | Honma et al. |
| 6,586,562 | B2 | 7/2003 | Honma et al. |
| 6,649,381 | B1 | 11/2003 | Honma et al. |
| 6,660,516 | B1 | 12/2003 | Imamura et al. |
| 6,686,439 | B2 | 2/2004 | Kenmoku et al. |
| 6,803,444 | B2 | 10/2004 | Suzuki et al. |
| 6,808,854 | B2 | 10/2004 | Imamura et al. |
| 6,828,074 | B2 | 12/2004 | Yano et al. |
| 6,853,477 | B2 | 2/2005 | Nomoto et al. |
| 6,855,472 | B2 | 2/2005 | Imamura et al. |
| 6,858,367 | B2 | 2/2005 | Yano et al. |
| 6,858,417 | B2 | 2/2005 | Yano et al. |
| 6,861,496 | B2 | 3/2005 | Kenmoku et al. |
| 6,861,550 | B2 | 3/2005 | Honma et al. |
| 6,864,074 | B2 | 3/2005 | Yano et al. |
| 6,867,023 | B2 | 3/2005 | Honma et al. |
| 6,869,782 | B2 | 3/2005 | Kenmoku et al. |
| 6,908,720 | B2 | 6/2005 | Kenmoku et al. |
| 6,916,861 | B2 | 7/2005 | Nomoto et al. |
| 6,951,745 | B2 | 10/2005 | Nomoto et al. |
| 7,153,622 | B2 | 12/2006 | Honma et al. |
| 7,169,598 | B2 | 1/2007 | Honma et al. |
| 7,235,396 | B2 | 6/2007 | Nomoto et al. |
| 7,267,974 | B2 | 9/2007 | Kozaki et al. |
| 7,354,995 | B2 | 4/2008 | Imamura et al. |
| 7,399,644 | B2 | 7/2008 | Honma et al. |
| 7,521,250 | B2 | 4/2009 | Hamachi |
| 7,524,659 | B2 | 4/2009 | Nomoto et al. |
| 7,527,963 | B2 | 5/2009 | Nomoto et al. |
| 2003/0194443 | A1 | 10/2003 | Yano et al. |
| 2005/0148086 | A1* | 7/2005 | Hamachi ............... 436/86 |
| 2007/0131546 | A1 | 6/2007 | Nomoto et al. |
| 2007/0131547 | A1 | 6/2007 | Nomoto et al. |
| 2008/0269065 | A1* | 10/2008 | Lyon et al. ............ 506/9 |
| 2009/0061498 | A1 | 3/2009 | Nomoto et al. |

FOREIGN PATENT DOCUMENTS

| | | |
|---|---|---|
| JP | 5-506432 A | 9/1993 |
| JP | 6-181890 A | 7/1994 |
| JP | 6-239893 A | 8/1994 |
| JP | 2003-246788 A | 9/2003 |
| JP | 2004-67659 | 3/2004 |

OTHER PUBLICATIONS

Ojida, Akio, et al. "Design and synthesis of bis(Zn(II)-dipicolylamine)-based fluorescent artificial chemosensors for phosphorylated proteins/peptides." Bulletin of the Chemical Society of Japan (2006) 79 p. 35-46.*

Koutaka, Hitomi, et al. "A novel fluorescent probe for zinc ion based on boron dipyrromethene (BODIPY) chromophore." Chemical and Pharmaceutical Bulletin (2004) 52 p. 700-703.*

Ojida, Akio, et al. "First artificial receptors and chemosensors toward phosphorylated peptide in aqueous solution." Journal of the American Chemical Society (2002) 124 p. 6256-6258.*

Martin, Karen, et al. "Strategies and solid-phase formats for the analysis of protein and peptide phosphorylation employing a novel fluorescent phosphorylation sensor dye." Combinatorial Chemistry and High Throughput Screening (2003) 6 p. 331-339.*

Ahrens, et al. "In vivo imaging platform for tracking immunotherapeutic cells", Nature Biotechnology, vol. 23, No. 8, Aug. 2005, pp. 983-987.

Grundke-Iqbal, et al., "Abnormal phosphorylation of the microtubule-associated protein T (tau) in Alzheimer cytoskeletal pathology", Proc. Natl. Acad. Sci., vol. 83, Jul. 1986, pp. 4913-4917.

Higuchi, et al., "19F and 1H MRI detection of amyloid β plaques in vivo", Nature Neuroscience, vol. 8, No. 4, Apr. 2005, pp. 527-533.

Ihara, et al., "Phosphorylated Tau Protein Is Integrated into Paired Helical Filaments in Alzheimer's Disease", J. Biochem., vol. 99, 1986, pp. 1807-1810.

Ishiguro, et al., "Phosphorylated tau in human cerebrospinal fluid is a diagnostic marker for Alzheimer's disease", Neuroscience Letters, vol. 270, 1999, pp. 91-94.

Itoh, et al., "Large-Scale, Multicenter Study of Cerebrospinal Fluid Tau Protein Phosphorylated at Serine 199 for the Antemortem Diagnosis of Alzheimer's Disease", Annals of Neurology, vol. 50, No. 2, 2001, pp. 150-156.

Mann, et al., "Analysis of protein phosphorylation using mass spectrometry: deciphering the phosphoproteome", Trends in Biotechnology, vol. 20, No. 6, Jun. 2002, pp. 261-268.

Mason, et al., "Perfluorocarbon Imaging in Vivo: A 19F MRI Study in Tumor-Bearing Mice", Magnetic Resonance Imaging, vol. 7, 1989, pp. 475-485.

Ojida, et al., "Cross-Linking Strategy for Molecular Recognition and Fluorescent Sensing of Multi-phosphorylated Peptide in Aqueous Solution", J. Am. Chem. Soc., vol. 125, 2003, pp. 10184-10185.

Okamura, et al., "Quinoline and Benzimidazole Derivatives: Candidate Probes for in Vivo Imaging of Tau Pathology in Alzheimer's Disease", The Journal of Neuroscience, vol. 25, No. 47, 2005, pp. 10857-10862.

Wolozin, et al., "Alzheimer-Related Neuronal Protein A68: Specificity and Distribution", Annals of Neurology, vol. 22, No. 4, 1987, pp. 521-526.

Yu, et al., "19F: A Versatile Reporter for Non-Invasive Physiology and Pharmacology Using Magnetic Resonance", Current Medicinal Chemistry, vol. 12, 2005, pp. 819-848.

* cited by examiner

Tau$_{210-220}$ 2P: AcHN-YSR<u>pT</u>Pp<u>S</u>LPTPPT-CONH$_2$    (SEQ ID NO: 1)
Tau$_{231-238}$ 2P: H$_2$N-YTPPK<u>pS</u>P<u>pS</u>S-CONH$_2$    (SEQ ID NO: 2)
Tau$_{227-238}$ 2P: H$_2$N-YAVVR<u>pT</u>PPK<u>pS</u>PSS-CONH$_2$    (SEQ ID NO: 3)
Tau$_{204-216}$ 3P: H$_2$N-YGTPG<u>pS</u>RSR<u>pT</u>P<u>pS</u>LPT-CONH$_2$    (SEQ ID NO: 4)
Tau$_{204-216}$ 2P (i, i+4): H$_2$N-YGTPG<u>pS</u>RSR<u>pT</u>PSLPT-CONH$_2$    (SEQ ID NO: 5)
Tau$_{204-216}$ 2P (i, i+6): H$_2$N-YGTPG<u>pS</u>RSRTP<u>pS</u>LPT-CONH$_2$    (SEQ ID NO: 6)

FIG. 7A

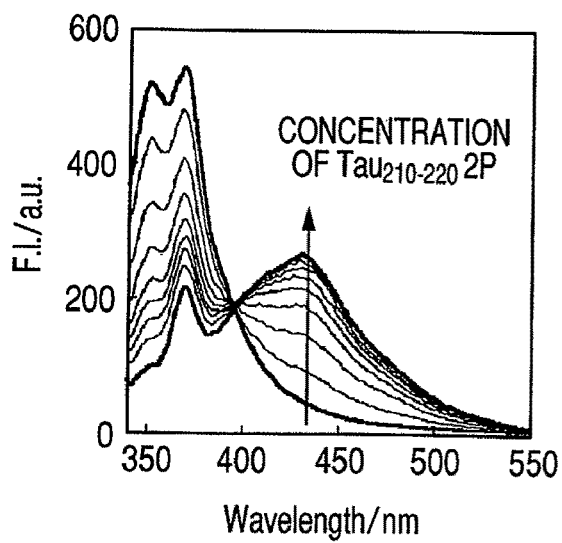

FIG. 7B

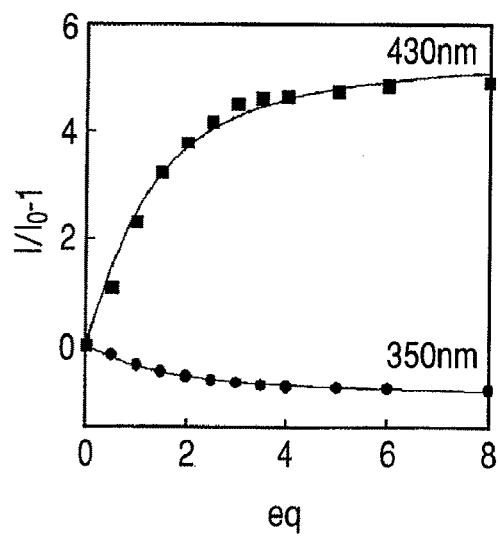

FIG. 8A
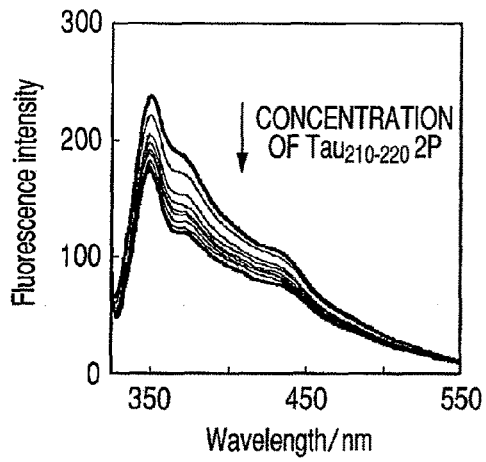
FIG. 8B
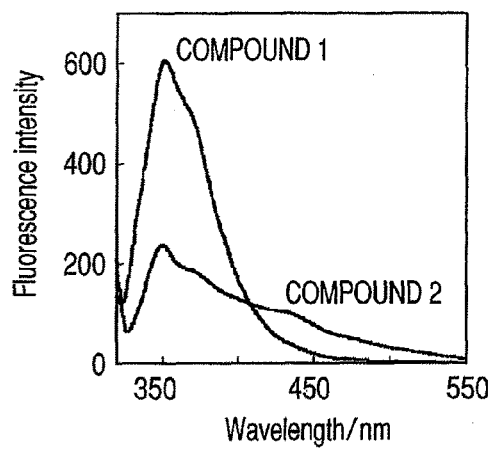
FIG. 9
| Peptide | DISTANCE BETWEEN PHOSPHATE GROUPS | $\lambda_{em}$ = 350nm | $\lambda_{em}$ = 430nm |
|---|---|---|---|
| $Tau_{210-220}$ 2P | i, i+2 | $1.03 \times 10^5$ M$^{-1}$ | $1.50 \times 10^5$ M$^{-1}$ |
| $Tau_{204-216}$ 3P | i, i+4, i+6 | $1.74 \times 10^5$ M$^{-1}$ | $8.98 \times 10^4$ M$^{-1}$ |
| $Tau_{204-216}$ 2P (i, i+4) | i, i+4 | —* | —* |
| $Tau_{204-216}$ 2P (i, i+6) | i, i+6 | —* | —* |
| $Tau_{231-238}$ 2P | i, i+2 | $5.95 \times 10^4$ M$^{-1}$ | $5.97 \times 10^4$ M$^{-1}$ |
| $Tau_{227-238}$ 2P | i, i+4 | —* | —* |
| PhP | — | —* | —* |
*No Fluorescence change was observed.

| Peptide | Tau$_{210-220}$ 2P | Tau$_{204-216}$ 3P | Tau$_{204-216}$ 2P (i, i+6) |
|---|---|---|---|
| N | 0.99 | 0.96 | 0.51 |
| K | $3.33 \times 10^5$ | $2.88 \times 10^5$ | $5.70 \times 10^3$ |
| ΔH | 10.7 | 9.92 | 15.5 |
| TΔS | 18.2 | 17.4 | 20.6 |

FIG. 15
Tau 0P: H2N-Tyr227-Ala-Val-Val-Arg-Thr-Pro-Pro-Lys-Ser-Pro-Ser-Ser238-amide    (SEQ ID NO: 7)
Tau 1P: H2N-Tyr227-Ala-Val-Val-Arg-Thr-Pro-Pro-Lys-pSer-Pro-Ser-Ser238-amide    (SEQ ID NO: 8)
Tau 2P: H2N-Tyr227-Ala-Val-Val-Arg-pThr-Pro-Pro-Lys-pSer-Pro-Ser-Ser238-amide    (SEQ ID NO: 9)
FIG. 16A
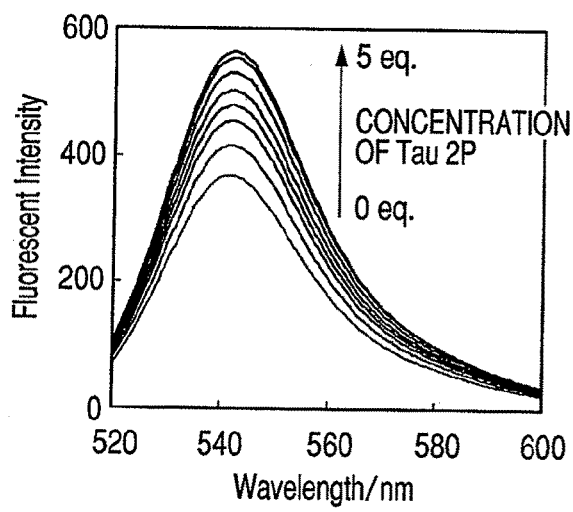
FIG. 16B
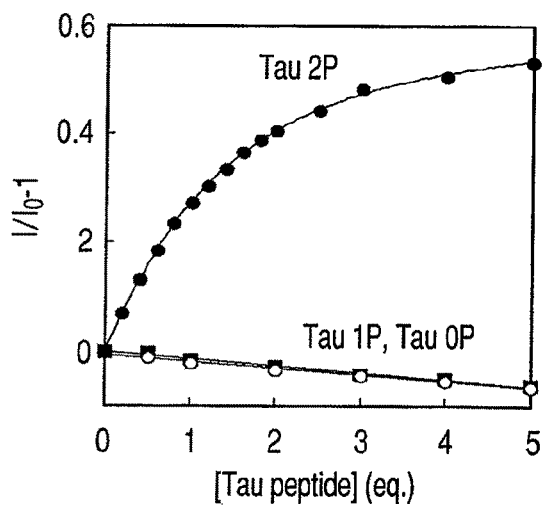
FIG. 17
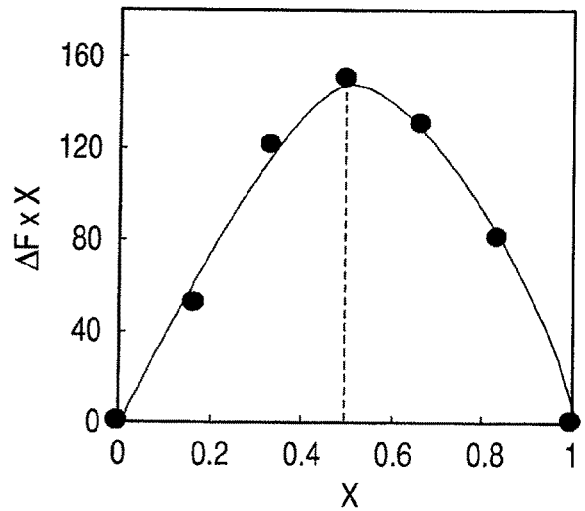

FIG. 22
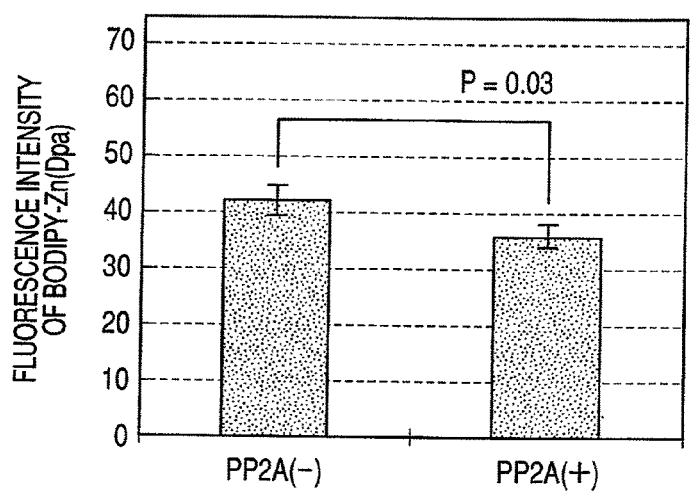
FIG. 23
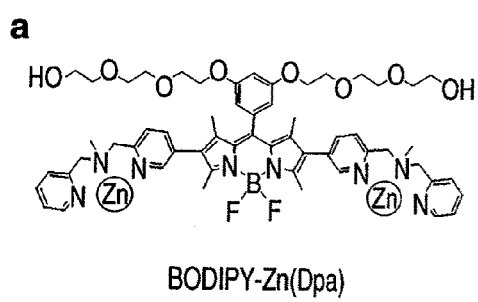
a
BODIPY-Zn(Dpa)
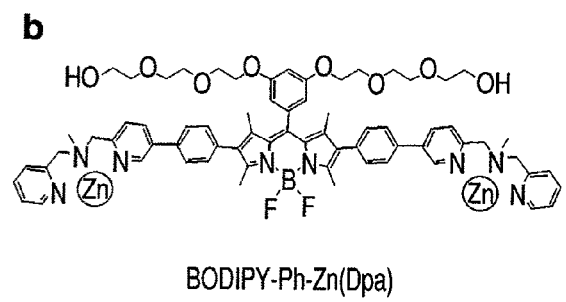
b
BODIPY-Ph-Zn(Dpa)
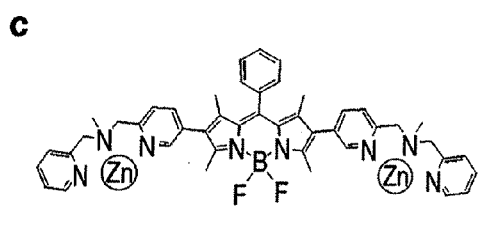
c
BODIPY-Zn(Dpa)EG0
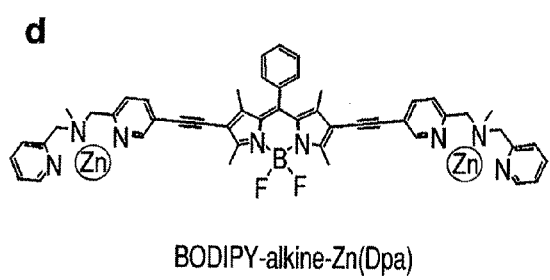
d
BODIPY-alkine-Zn(Dpa)

BODIPY-Zn(Dpa)  BODIPY-Ph-Zn(Dpa)  BODIPY-Zn(Dpa)EG0  BODIPY-alkine-Zn(Dpa)

MAXIMUM ABSORPTION WAVELENGTHS AND PARTITION COEFFICIENTS $P_{ow}$ (OCTANOL/WATER) OF Zn/Dpa BINUCLEAR COMPLEX COMPOUNDS a TO d

| compound | | Abs.max. | $P_{ow}(C_{oct.}/C_{water})$ |
|---|---|---|---|
| a | BODIPY-Zn(Dpa) | 523nm | 1.98 |
| b | BODIPY-Ph-Zn(Dpa) | 526nm | 20.43 |
| c | BODIPY-Zn(Dpa)EG0 | 517nm | 11.54 |
| d | BODIPY-alkine-Zn(Dpa) | 593nm | 2.78 |

SEQUENCE LISTING

```
<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: Tauprotein(210-220)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: PHOSPHORYLATION
<222> LOCATION: (4)..(4)
<220> FEATURE:
<221> NAME/KEY: PHOSPHORYLATION
<222> LOCATION: (6)..(6)
<220> FEATURE:
<221> NAME/KEY: MOD_RES
<222> LOCATION: (12)..(12)
<223> OTHER INFORMATION: AMIDATION

<400> SEQUENCE: 1

Tyr Ser Arg Thr Pro Ser Leu Pro Thr Pro Pro Thr
1               5                   10

<210> SEQ ID NO 2
<211> LENGTH: 9
<212> TYPE: PRT
<213> ORGANISM: Artificial Sequence
```

```
<220> FEATURE:
<223> OTHER INFORMATION: Tauprotein(231-238)
<220> FEATURE:
<221> NAME/KEY: PHOSPHORYLATION
<222> LOCATION: (6)..(6)
<220> FEATURE:
<221> NAME/KEY: PHOSPHORYLATION
<222> LOCATION: (8)..(8)
<220> FEATURE:
<221> NAME/KEY: MOD_RES
<222> LOCATION: (9)..(9)
<223> OTHER INFORMATION: AMIDATION

<400> SEQUENCE: 2

Tyr Thr Pro Pro Lys Ser Pro Ser Ser
1               5

<210> SEQ ID NO 3
<211> LENGTH: 13
<212> TYPE: PRT
<213> ORGANISM: Artificial Sequence
<220> FEATURE:
<223> OTHER INFORMATION: Tauprotein(227-238)
<220> FEATURE:
<221> NAME/KEY: PHOSPHORYLATION
<222> LOCATION: (6)..(6)
<220> FEATURE:
<221> NAME/KEY: PHOSPHORYLATION
<222> LOCATION: (10)..(10)
<220> FEATURE:
<221> NAME/KEY: MOD_RES
<222> LOCATION: (13)..(13)
<223> OTHER INFORMATION: AMIDATION

<400> SEQUENCE: 3

Tyr Ala Val Val Arg Thr Pro Pro Lys Ser Pro Ser Ser
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Tauprotein(204-216)
<220> FEATURE:
<221> NAME/KEY: PHOSPHORYLATION
<222> LOCATION: (6)..(6)
<220> FEATURE:
<221> NAME/KEY: PHOSPHORYLATION
<222> LOCATION: (10)..(10)
<220> FEATURE:
<221> NAME/KEY: PHOSPHORYLATION
<222> LOCATION: (12)..(12)
<220> FEATURE:
<221> NAME/KEY: MOD_RES
<222> LOCATION: (15)..(15)
<223> OTHER INFORMATION: AMIDATION

<400> SEQUENCE: 4

Tyr Gly Thr Pro Gly Ser Arg Ser Arg Thr Pro Ser Leu Pro Thr
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Tauprotein(204-216)
<220> FEATURE:
<221> NAME/KEY: PHOSPHORYLATION
<222> LOCATION: (6)..(6)
<220> FEATURE:
<221> NAME/KEY: PHOSPHORYLATION
<222> LOCATION: (10)..(10)
```

```
<220> FEATURE:
<221> NAME/KEY: MOD_RES
<222> LOCATION: (15)..(15)
<223> OTHER INFORMATION: AMIDATION

<400> SEQUENCE: 5

Tyr Gly Thr Pro Gly Ser Arg Ser Arg Thr Pro Ser Leu Pro Thr
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Tauprotein(204-216)
<220> FEATURE:
<221> NAME/KEY: PHOSPHORYLATION
<222> LOCATION: (6)..(6)
<220> FEATURE:
<221> NAME/KEY: PHOSPHORYLATION
<222> LOCATION: (12)..(12)
<220> FEATURE:
<221> NAME/KEY: MOD_RES
<222> LOCATION: (15)..(15)
<223> OTHER INFORMATION: AMIDATION

<400> SEQUENCE: 6

Tyr Gly Thr Pro Gly Ser Arg Ser Arg Thr Pro Ser Leu Pro Thr
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Tauprotein(227-238)
<220> FEATURE:
<221> NAME/KEY: MOD_RES
<222> LOCATION: (13)..(13)
<223> OTHER INFORMATION: AMIDATION

<400> SEQUENCE: 7

Tyr Ala Val Val Arg Thr Pro Pro Lys Ser Pro Ser Ser
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Tauprotein(227-238)
<220> FEATURE:
<221> NAME/KEY: PHOSPHORYLATION
<222> LOCATION: (10)..(10)
<220> FEATURE:
<221> NAME/KEY: MOD_RES
<222> LOCATION: (13)..(13)
<223> OTHER INFORMATION: AMIDATION

<400> SEQUENCE: 8

Tyr Ala Val Val Arg Thr Pro Pro Lys Ser Pro Ser Ser
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Tauprotein(227-238)
<220> FEATURE:
<221> NAME/KEY: PHOSPHORYLATION
<222> LOCATION: (6)..(6)
```

```
<220> FEATURE:
<221> NAME/KEY: PHOSPHORYLATION
<222> LOCATION: (10)..(10)
<220> FEATURE:
<221> NAME/KEY: MOD_RES
<222> LOCATION: (13)..(13)
<223> OTHER INFORMATION: AMIDATION

<400> SEQUENCE: 9

Tyr Ala Val Val Arg Thr Pro Pro Lys Ser Pro Ser Ser
1               5                   10
```

MULTISITE PHOSPHORYLATED PEPTIDE (PROTEIN) RECOGNIZING COMPOUND AND DETECTION METHOD, IMAGING METHOD, ALZHEIMER'S DISEASE DIAGNOSING METHOD AND REAGENT KIT USING THE SAME

BACKGROUND OF THE INVENTION

1. Field of the Invention

The present invention relates to a compound for detecting a phosphorylated peptide or protein that recognizes a phosphate group at multiple sites. Furthermore, the present invention relates to a method for detecting a multisite phosphorylated peptide or protein in a sample using the compound. In particular, the present invention relates to a compound that specifically recognizes an excessively phosphorylated tau protein, a method for detecting a phosphorylated tau protein in a sample using the compound, and a method for detecting Alzheimer's disease, an imaging method, a method for diagnosing Alzheimer's disease and a reagent kit using the compound.

2. Description of the Related Art

Proteins in the body are subjected to various biochemical modifications and change their higher-order structures, functions and activities to regulate biological function. Protein phosphorylation, one of protein modifications, is a posttranslational modification catalyzed by protein phosphorylating enzymes (protein kinases) using ATP as a phosphate group donor. Protein phosphorylation is closely associated with various cellular activities such as carbohydrate metabolism, cell growth/division, intracellular signal transduction, and enzyme activity regulation. Protein phosphorylation is an important process for regulating protein activity, and it is estimated that approx. 30% of proteins are subjected to phosphorylation in some manner in eukaryotes (for example, refer to Matthias Mann et al., Trends Biotechnol. [2002] 20, 261-268). Phosphorylation states in the body are strictly regulated by protein phosphorylating enzymes (kinases) and dephosphorylating enzymes (phosphatases) to maintain normal physiological functions. It has been reported that abnormal regulation of phosphorylation causes various diseases including cancer. Drugs for regulating phosphorylation have been searched, and several kinase inhibitors have been clinically applied.

Alzheimer's disease is known as one of diseases characterized by abnormally phosphorylated proteins as pathological changes. Alzheimer's disease is one of diseases difficult to treat, and studies aiming for correct early diagnoses and early treatment have been conducted. As a pathological characteristic of Alzheimer's disease, senile plaques and neurofibrillary tangles are confirmed in the patient's brain. The neurofibrillary tangle is accumulation of a double-helical fibrous protein called paired helical filament (PHF) in the nerve cell. One of its components is a tau protein, one of microtubule-associated proteins specific to the brain (for example, refer to Yasuo Ihara et al., Journal of Biochemistry [Tokyo], [1986] 99, 1807-1810 and Inge Grundke-Iqbal et al., Proc. Natl. Acad. Sci. USA 83, 4913-4917). It has been found that the tau proteins incorporated in PHFs in the brain affected by Alzheimer's disease are abnormally phosphorylated as compared with normal tau proteins, and their phosphorylation sites have been identified (for example, refer to Japanese Patent Application Laid-Open No. 6-239893). In addition to Alzheimer's disease, diseases that present accumulation of tau proteins in the brain as the principal sign (tauopathies) include Pick disease, progressive supranuclear palsy, and frontotemporal dementia, and all these diseases are closely associated with phosphorylated tau proteins. Therefore, detection, in vivo or in vitro, of a phosphorylated tau protein as a marker is one of excellent methods for diagnosing diseases characterized by accumulation of phosphorylated tau proteins, in particular, Alzheimer's disease.

As described above, the consensus is that monitoring of phosphorylation of proteins closely associated with a disease is very important and effective in the fields of biomedical studies, laboratory tests, and in-vivo image diagnoses. To achieve this monitoring with high sensitivity and high precision, it is necessary to develop compound molecules for monitoring phosphorylated proteins specifically with high sensitivity and techniques for detecting these proteins.

SUMMARY OF THE INVENTION

Compounds for detecting a phosphorylated protein in any form used in vitro or in vivo have been discussed in the literature. In general, methods using radioactive isotopes, methods using antibodies, and methods utilizing changes in physicochemical property after phosphorylation have been employed in vitro. In a method using a radioactive isotope, for example, cells are allowed to take up $^{32}P$ and cultured, then extracted proteins are separated by electrophoresis, proteins are detected by Coomassie brilliant blue (CBB) staining, and the uptake of $^{32}P$ into proteins is detected by autoradiography to analyze the phosphorylation state. In this technique, phosphorylated proteins can be detected with high sensitivity, but facilities for using radioactive isotopes are required, and there are problems of cumbersome operations, exposure, and contamination. In a method using an anti-phosphorylated antibody, a protein sample is subjected to electrophoresis and then transferred to a membrane, and phosphorylated proteins are detected using an anti-phosphorylated antibody. This technique suffers from problems that an antibody recognizing a target protein must be obtained as a precondition, and cumbersome operations are required. A method utilizing a change in physicochemical property after phosphorylation, for example, uses a change in mobility in electrophoresis due to a change of the charge state of a whole protein caused by phosphorylation as an indicator. This detection method suffers from low precision.

Meanwhile, for the purpose of diagnoses of tau-accumulating diseases such as Alzheimer's disease, methods for quantifying tau proteins in the cerebrospinal fluid have been reported. For example, methods for confirming the presence of tau proteins in the cerebrospinal fluid using antibodies have been proposed (see, for example, Benjamin Wolozin et al., Annals of Neurology, [1987] 22, 521-526). Furthermore, methods for detecting Alzheimer's disease by focusing on phosphorylation sites of phosphorylated tau proteins in PHFs have been developed (see, for example, Koichi Ishiguro et al., Neuroscience Letters, [1999] 270, 91-94 and Nobuo Itoh et al., Annals of Neurology, [2001] 50, 150-156). Antibodies are excellent compounds in view of specificity, but costs for producing antibodies are problematic. Furthermore, in intracerebral imaging, poor delivery of antibodies into the brain is a serious problem since their molecular weights are as large as 150 kDa. In studies or diagnoses of Alzheimer's disease, brain sections from a patient with Alzheimer's disease are stained. Conventional staining agents, such as congo red and thioflavine S, are characterized by positivity for both intracerebral senile plaques and neurofibrillary tangles but cannot specifically stain tau proteins. Compounds with high specificity to tau proteins for quantifying tau proteins noninvasively in vivo have been discussed (refer to Japanese Patent Application Laid-Open No. 2004-67659). However, since the compounds disclosed in Japanese Patent Application Laid-Open No. 2004-67659 basically recognize a cross-beta structure and bind to a tau protein aggregate, these compounds also bind weakly to amyloid beta proteins, which similarly have a cross-beta structure. Therefore, low molecular weight organic compounds with high specificity to tau proteins for the diagnoses of diseases associated with accumulation of tau proteins, including Alzheimer's disease, have not been found.

Meanwhile, sequence-selective sensor compounds for phosphorylated peptides have been reported (for example, refer to Japanese Patent Application Laid-Open No. 2003-246788). Here, it is known that a zinc-dipicolylamine binuclear complex can fluorescently detect phosphate ions and phosphorylated peptides in an aqueous solution having physiological conditions. Furthermore, compounds that can recognize a multisite phosphorylated peptide using these compounds have also been reported (for example, refer to Akio Ojida et al., J. Am. Chem. Soc., [2003] 125, 10184-10185). These are compounds that can recognize a plurality of phosphate groups by interactions of crosslinked metal-ligand. However, since these compounds do not greatly change their affinity due to the difference in the distance between phosphate groups, it is difficult to recognize specific multisite phosphorylation sites using the distance between the phosphate groups as a reference. This appears to be because the distance between phosphate group recognition sites greatly changes due to the low molecular rigidity and high molecular mobility of the compounds.

In studies, diagnoses, and treatment of diseases caused by abnormal phosphorylation, such as abnormal phosphorylation of tau proteins in the brain affected by Alzheimer's disease, a compound that can specifically detect these abnormally phosphorylated proteins in vitro and in vivo and a convenient detection method using the compound are required.

Accordingly, objects of the present invention is to solve the problems of the prior art and provide a novel compound that captures a multisite phosphorylated protein or peptide specifically to phosphorylation sites and a method for detecting a multisite phosphorylated protein or peptide using the same. In particular, a compound that specifically detects excessively phosphorylated tau proteins observed in the brain affected by Alzheimer's disease and a method for diagnosing Alzheimer's disease in vitro or in vivo using the compound.

To achieve the above-mentioned objects, the inventors of the present invention conducted various researches about novel compounds and methods for detecting multisite phosphorylated proteins or peptides rapidly with favorable sensitivity, and accomplished the present invention, which detects a multisite phosphorylated protein or peptide.

The compound for detecting a phosphorylated protein or peptide of the present invention can detect a captured phosphorylated substance specifically and rapidly with high sensitivity because the compound of the present invention can recognize phosphorylation sites of the protein or peptide specifically to the distance between the phosphorylation sites and bind to the peptide. As a result of the binding of the compound and the protein or peptide, a chromogenic or luminescent change is induced in the compound, and the phosphorylated protein or peptide can be detected or a kinase activity can be measured with high sensitivity by measuring this change. Since the compound of the present invention has a property of selectively recognizing a protein or peptide phosphorylated at multiple specific sites and binding to the phosphorylated protein or peptide, the compound of the present invention can also be used as means for isolating or purifying a multisite phosphorylated protein or peptide. The compound for detecting a phosphorylated protein or peptide of the present invention also has a potential as a molecular tool for elucidating intracellular signal transduction mechanisms or as an inhibitor of an interaction between proteins via a specific phosphate group. The present invention provides a novel compound for detecting an excessively phosphorylated tau protein utilizing ability to specifically recognize a phosphorylated protein or peptide and a method for diagnosing Alzheimer's disease using the same.

Further features of the present invention will become apparent from the following description of exemplary embodiments with reference to the attached drawings.

BRIEF DESCRIPTION OF THE DRAWINGS

FIG. 6 illustrates a partial sequence peptide of a synthesized phosphorylated tau protein. The underline represents a phosphorylation residue.

FIG. 7A illustrates changes in fluorescence of compound 1 (10 μM) with dropwise addition of $Tau_{210-220}2P$. FIG. 7B illustrates a titration plot at each wavelength ($\lambda_{em}$=350 nm: closed circle, $\lambda_{em}$=430 nm: closed square).

FIG. 8A illustrates changes in fluorescence of compound 2 (10 μM) with dropwise addition of $Tau_{210-220}2P$. FIG. 8B illustrates a comparison between compounds 1 and 2 in fluorescence spectra.

FIG. 9 is a table showing a binding constant at each wavelength after various peptides were added dropwise to compound 1.

FIG. 15 illustrates a partial sequence peptide of a synthesized phosphorylated tau protein.

FIG. 16A illustrates changes in fluorescence of BODIPY-Zn(Dpa) (5 μM) with dropwise addition of Tau 2P. FIG. 16B illustrates changes in fluorescence intensity after addition of Tau 0P (open circle), Tau 1P (closed square) and Tau 2P (closed square).

FIG. 17 illustrates a Job's plot about formation of a complex of BODIPY-Zn(Dpa) and Tau 2P. Here, [BODIPY-Zn(Dpa)]+[Tau 2P]=5 μM, χ=[BODIPY-Zn(Dpa)]/{[BODIPY-Zn(Dpa)]+[Tau 2P]}.

FIG. 22 illustrates changes in fluorescence intensity of BODIPY-Zn(Dpa) in a hippocampal tissue section from the human brain affected by Alzheimer's disease (AD) after treatment with a dephosphorylating enzyme (PP2A).

FIG. 23 illustrates structural formulas of Zn/Dpa binuclear complex compounds a to d containing BODIPY-Zn(Dpa).

FIG. 26A is HPLC chart when the homogenate solution of the brain at 2 min after administration was injected and FIG. 26B shows HPLC chart when the homogenate solution of the brain at 30 min after administration was injected. The peak of BODIPY-Zn(Dpa) can be seen at 16 to 18 minutes in retention time.

DESCRIPTION OF THE EMBODIMENTS

Figure 1:
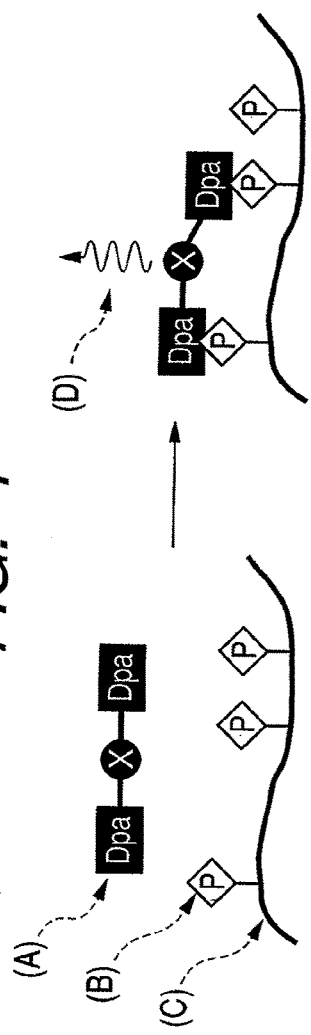
FIG. 1 is a schematic view illustrating the method for detecting a phosphorylated protein or peptide using the multisite phosphate group-recognizing compound provided by the present invention (P represents a phosphate group, and X represents a spacer between two Dpa's).

The compound of the present invention is a compound having a structure including two 2,2'-dipicolylamine (Dpa) moieties and a spacer X, represented by the following formula (1):

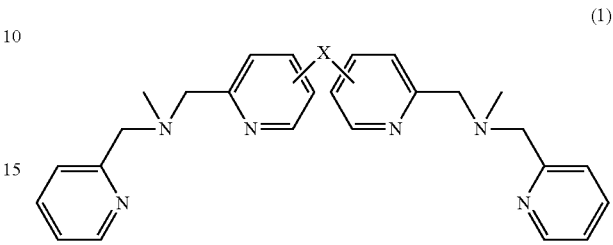

(1)

wherein a hydrogen atom in the Dpa may be replaced by an atom or an atom group other than hydrogen.

In the formula (1) representing the compound of the present invention, X constitutes a spacer site. The spacer X solely or taken together with at least one of the pyridine rings to which the spacer X binds has a chromogenic or luminescent functional group or atom group. X can have such a structure that the distance between two pyridine rings to which the spacer X binds should not change. Examples of X can be represented by the following formulas (2) to (5):

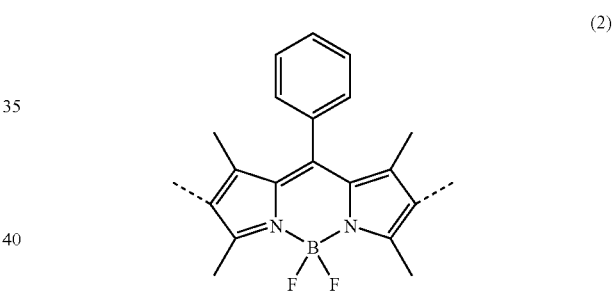

(2)

wherein the dotted line represents a site at which the spacer X binds to a pyridine ring in the Dpa, and a hydrogen atom in the phenyl group may be replaced by an atom or an atom group other than hydrogen;

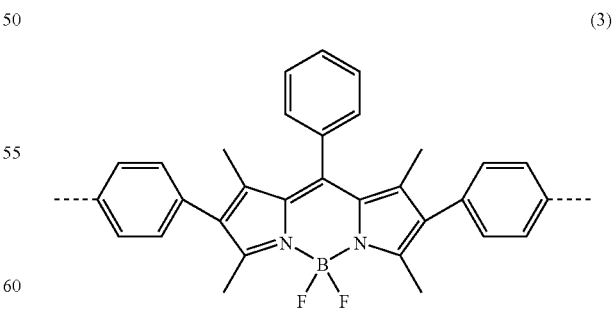

(3)

wherein the dotted line represents a site at which the spacer X binds to a pyridine ring in the Dpa, and a hydrogen atom in the phenyl group and/or a hydrogen atom in the phenylene group may be replaced by an atom or an atom group other than hydrogen;

(4)

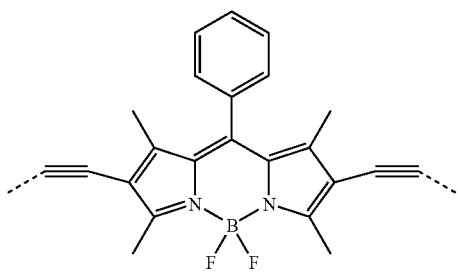

wherein the dotted line represents a site at which the spacer X binds to a pyridine ring in the Dpa, and a hydrogen atom in the phenyl group may be replaced by an atom or an atom group other than hydrogen; and (5)

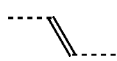

wherein the dotted line represents a site at which the spacer X binds to a pyridine ring in the Dpa.

Furthermore, the compound represented by the formula (1) may have any of an ethylene glycol chain, a luminescent substance, a chromogenic substance, a nuclear magnetic resonance-active nuclide, a paramagnetic substance, a magnetic particle, a γ-ray-emitting nuclide and a positron-emitting nuclide. For example, a hydrogen atom in the Dpa, a hydrogen atom in the spacer X or a hydrogen atom in the phenyl group and/or a hydrogen atom in the phenylene group in the compound represented by the formula (1) may be replaced by any of an ethylene glycol chain, a luminescent substance, a chromogenic substance, a nuclear magnetic resonance-active nuclide, a paramagnetic substance, a magnetic particle, a γ-ray-emitting nuclide and a positron-emitting nuclide.

Dpa can form a complex with a metal M. For example, a transition metal such as Zn, Ni, Fe, Co or Mn can serve as a ligand. Such a metal complex compound is a metal complex compound having a structure represented by the following general formula (6), in which dipicolylamine (Dpa) forms a complex with a metal M, wherein X represents a spacer molecule, and a hydrogen atom in the Dpa may be replaced by an atom or an atom group other than hydrogen:

(6)

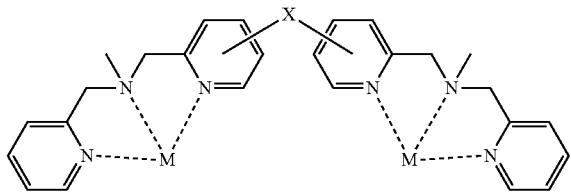

A preferred example of the metal complex compound of the present invention which recognizes a multisite phosphorylated protein or peptide can be a compound in which two zinc complex compounds each including Dpa and zinc (also referred to as a phosphate group-recognizing zinc complex site) are linked to each other with spacer X as represented by the following general formula (formula 7).

In this case, Dpa is a terdentate ligand and shows high affinity for zinc ion having a tetrahedral structure. One ligand of zinc ion is vacant. The compound of the formula (7) exists as a salt of a functional group or an atom group that is eliminated and becomes an anion in an aqueous solution. Examples of counter ions include $NO_3$, halogen atoms (in particular, chlorine and bromine), $ClO_4$ (perchlorate ion) and so forth.

(7)

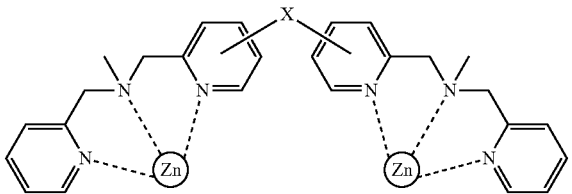

The zinc complex compound of Dpa in the formula (7) can be a phosphate group-selective luminescent compound which shows a marked change in fluorescence in an aqueous solution with neutral pH corresponding to a condition in the body (physiological condition) in the presence of a phosphate anion (refer to Japanese Patent Application Laid-Open No. 2003-246788). This appears to be because the zinc complex compound of Dpa selectively captures phosphate anion in water after a counter ion is eliminated and replaced with a phosphate anion, and this is observed as a change in fluorescence. Thus, the luminescent compound represented by the formula (7) of the present invention similarly functions as a compound with high sensitivity to a multisite phosphorylated peptide that shows a clear change in fluorescence in the presence of a multisite phosphorylated peptide having a very low concentration in the order of μM (see the examples described later).

In the formula (7) representing the compound of the present invention, X constitutes a spacer site. The spacer X solely or taken together with at least one of the pyridine rings to which the spacer X binds has a chromogenic or luminescent functional group or atom group. More preferably, the spacer X has such a structure that the distance between two pyridine rings to which the spacer X binds should not change. Examples of the spacer X can be represented by the following (8) to (11). Furthermore, the spacer X links pyridine rings of two Dpa, so that the compound can recognize two phosphate groups distance-selectively.

This X serving as a spacer is preferably a molecule with rigidity. Rigidity is a very important factor in the multisite recognition of phosphate groups. The term "rigidity" used herein means that bonds between atoms constituting the spacer X are strong, and X is not rotational in the molecule and has a molecular structure with a minimal extension. Therefore, the spacer X has a planar structure, and a functional group or a compound having the π-conjugated system such as, for example, a carbon-carbon double bond, a carbon-carbon triple bond, an aromatic ring, stilbene, naphthalimide, perylene, coumarin, fluorescein, rhodamine, cyanine dye, and BODIPY pigment can be used to impart rigidity. Rotation of the spacer greatly changes the distance between two Zn atoms. Furthermore, as discussed in Japanese Patent Application Laid-Open No. 2003-246788, the distance between two Zn atoms is greatly changed by molecular motion or rotational motion of a methylene chain in a compound in which a Zn/Dpa complex is linked to the spacer via methyl- (8)

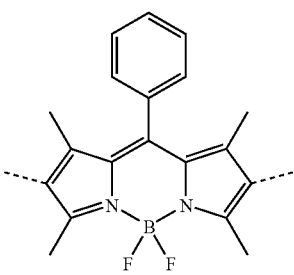

In the formula (8), the dotted line represents a site at which the spacer X binds to a pyridine ring in the Dpa, and a hydrogen atom in the phenyl group may be replaced by an atom or an atom group other than hydrogen;

(9)

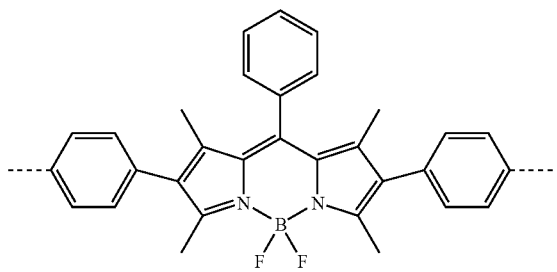

In the formula (9), the dotted line represents a site at which the spacer X binds to a pyridine ring in the Dpa, and a hydrogen atom in the phenyl group and/or a hydrogen atom in the phenylene group may be replaced by an atom or an atom group other than hydrogen;

(10)

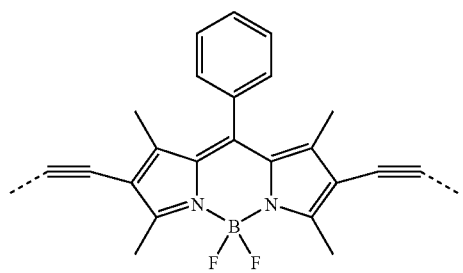

In the formula (10), the dotted line represents a site at which the spacer X binds to a pyridine ring in the Dpa, and a hydrogen atom in the phenyl group may be replaced by an atom or an atom group other than hydrogen; and

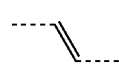

(11)

In the formula (11), the dotted line represents a site at which the spacer X binds to a pyridine ring in the Dpa.

The compound of the present invention can modify various functional molecules. As a modifying molecule, the compound of the present invention can modify molecules such as, for example, an ethylene glycol chain for improvement of water-solubility, chromogenic or luminescent substances such as, for example, luminol, isoluminol, luciferin, dioxetane, fluorescein and Rhodamine for luminescence/fluorescence sensing, paramagnetic substances, magnetic particles and nuclear magnetic resonance-active nuclides for detection by a nuclear magnetic resonance method, radionuclides such as $^{123}$I, $^{201}$Tl, $^{67}$Ga, $^{99m}$Tc and $^{111}$In, for detection of a γ-counter, positron-releasing nuclides such as $^{15}$O, $^{13}$N and $^{11}$C and $^{18}$F and drugs for therapeutic treatment. An ethylene glycol chain for improvement of water-solubility of the compound is particularly preferred. Further, gadolinium can be preferably used as a paramagnetic substance, and an iron oxide microparticle as a magnetic particle. Furthermore, $^{1}$H, $^{13}$C, $^{15}$N, $^{19}$F, $^{23}$Na, $^{29}$Si, $^{31}$P and the like can be preferably used as nuclear magnetic resonance-active nuclides.

Of these, $^{19}$F is an NMR nuclide having natural abundance of virtually 100% as with $^{1}$H, and the detection sensitivity is as high as 83% of $^{1}$H. Since a very small amount of fluorine is present in an organism, imaging using a molecule having $^{19}$F as a probe is enabled by using a fluorine-containing compound as a contrast medium (for example, refer to Japanese Patent Application Laid-Open No. H06-181890 and National Publication of International Patent Application No. H05-506432). Fluorine imaging enables measurement with a general-purpose MRI apparatus for $^{1}$H. Molecules having $^{19}$F are used as probes for analysis of changes in structures and interactions of proteins in addition to their in vivo use, and NMR and MRI using $^{19}$F as a detection nucleus (hereinafter may be referred to as F-NMR and F-MRI, respectively) are very useful both academically and clinically (for example, refer to Yu J X et al., Curr Med. Chem., 12, 819-848, 2005). For example, transplanted cells labeled with a perfluoro compound are detected in vivo (for example, refer to Ahrens E T et al., Nat. Biotechnol., 23, 983-987, 2005). Amyloid protein imaging of Alzheimer's disease (for example, refer to Higuchi M et al., Nat. Neurosci., 8, 527-533, 2005) and tumor imaging (for example, refer to Mason R P et al., Magnetic Resonance Imaging, 7, 475-485, 1989) have been reported. The above-mentioned modification of various functional molecules may be performed by substituting a hydrogen atom in the Dpa or substituting a hydrogen atom in the spacer X or a hydrogen atom in the phenyl group and/or a hydrogen atom in the phenylene group.

Thus, particularly preferred examples of the compound for detecting a phosphorylated protein or peptide of the present invention are represented by the following formulas (12) to (16). The compound represented by the formula (12) is an example in which a hydrogen atom in the phenyl group in the formula (2) or (8) is replaced. The compound of the formula (14) is an example in which a hydrogen atom in the phenyl group in the formula (3) or (9) is replaced.

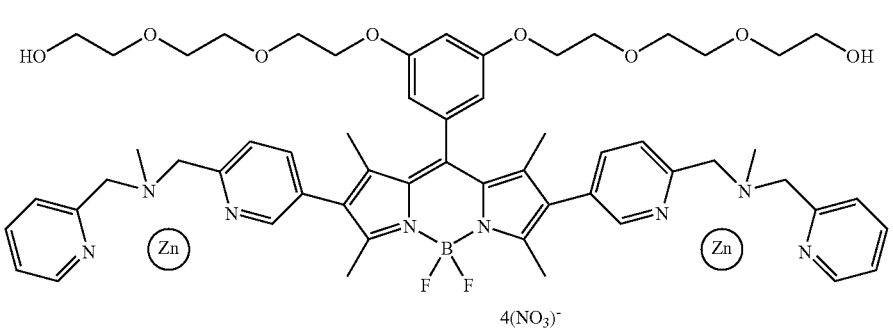

(12)

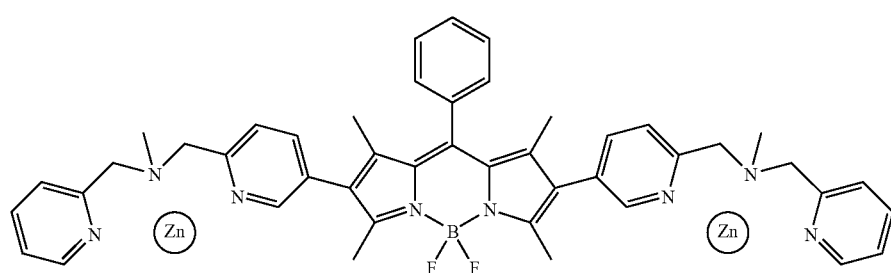

(13)

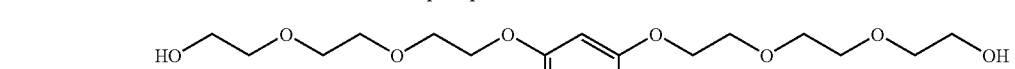

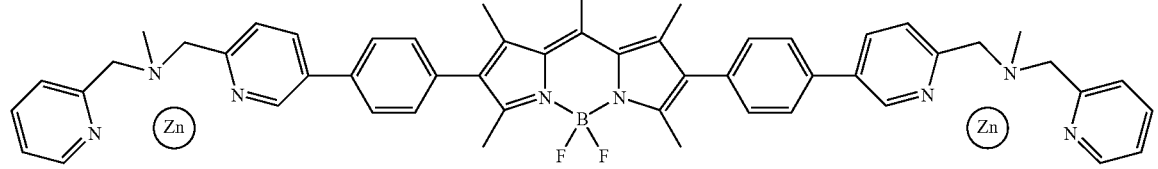

(14)

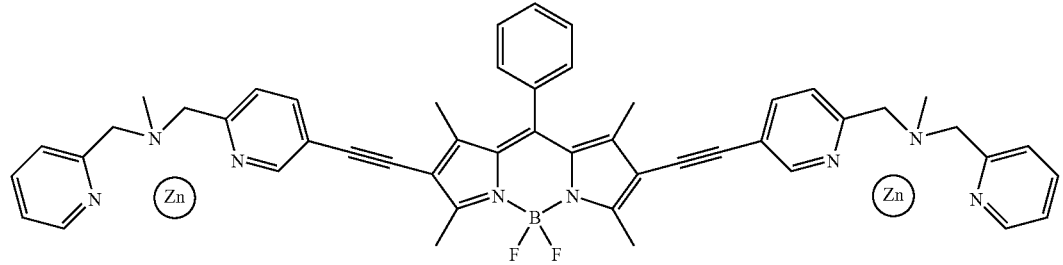

(15)

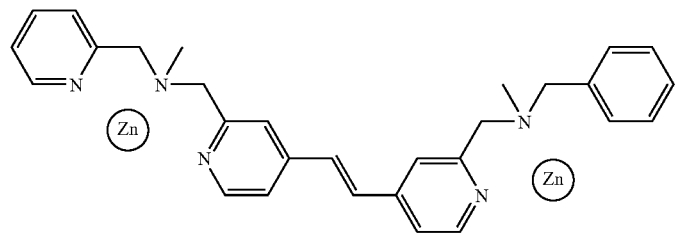

(16)

The compound of the present invention of such a zinc binuclear complex type has a function of selectively recognizing and capturing a protein or peptide having phosphorylated residues with a specific distance depending on the distance set by the spacer X because zinc having a vacancy as described above specifically binds to the phosphate groups in the protein or peptide. For example, the type having a stilbazole skeleton using a vinyl group as a spacer represented by the above-mentioned formula (16) selectively recognizes a protein or peptide having a sequence including phosphorylated amino acids at the ith and i+2th multisite phosphorylation sites (see Example 1 described later). A zinc binuclear complex having a BODIPY skeleton as a spacer represented by the above-mentioned formula (12) can have a favorable ability of recognizing a protein or a peptide having a sequence including phosphorylated amino acids at the ith and i+4th multisite phosphorylation sites (see Example 2 described later). Neither of these compounds binds to an unphosphorylated peptide or a peptide having only one phosphorylated amino acid. Thus, the compound of the present invention recognizes a specific phosphorylated protein or peptide, that is, a protein or peptide having phosphate groups at specific positions, in water, recognizes the protein or peptide between two phosphate groups by crosslinking after the binding of zinc to each phosphate group as a ligand, and then captures the protein or peptide by forming a complex of 1:1. These findings have been confirmed by measuring the circular dichroism (CD) spectrum as shown in the examples described later. That is, the metal complex compound of the present invention can detect a multisite phosphorylated peptide or protein.

In the method for detecting a phosphorylated peptide (protein) of the present invention, the compound of the present invention is brought into contact with a phosphorylated peptide (protein) to form a complex of the compound and the phosphorylated peptide (protein), and the complex is detected. Here, the complex may be formed by crosslinking the compound to a phosphate group of the phosphorylated peptide or protein. Detection can be performed by measuring a change in an optical signal such as a fluorescence signal or a luminescence signal emitted by the compound after the binding, which is induced by formation of the complex. Furthermore, a structural change on the side of the phosphorylated peptide or protein, a substance to be captured, may be detected by optical detection methods using circular dichroism (CD) or the like. The detection methods are not limited to these methods, and a labeled substance that can emit a signal such as a fluorescent substance or a luminescent substance, an enzyme, a fluorescent protein, a luminescent protein, a magnetic substance, a conductive substance, or the like can be introduced into the spacer X and can be observed with an appropriate detection system after an interaction with a phosphorylated peptide. In addition to direct measurement of these substances, the compound may be detected by secondarily binding a substance that can emit a signal such as fluorescence specifically to the compound of the present invention and detecting the signal. In this case, a compound that captures a phosphorylated peptide is detected with a fluorescence spectrophotometer, a γ-counter or the like by detecting a signal such as light or radiation emitted from a substance used for labeling. The labeled substances are not limited, and known labeled substances listed below and derivatives or adducts thereof can be used. Examples of fluorescence-labeled substances include Alexa-350, Cy2, BODIPY 505/515, fluorescein isothiocyanate (FITC), eosin isothiocyanate, Alexa-488, Alexa-430, Alexa-532, Alexa-555, Cy3, Alexa-546, PE, Rhodamine B, Cy3.5, Alexa-568, BODIPY 580/605, Alexa-594, Texas Red, Alexa-633, APC, Alexa-647, Cy5, Alexa-660, Alexa-680, Cy5.5, Alexa-750, Cy7, indocyanine green, lanthanoid complexes such as europium and samarium and so forth. Examples of luminescence-labeled substances include luminol, isoluminol, luciferin, dioxetane, lucigenin (bis-N-methylacridinium nitrate), acridinium esters, adamantyl-1,2-dioxetane allyl phosphate, nitric oxide, bis(2,4,6-trichlorophenyl)oxalate and so forth. Furthermore, combinations of an enzyme and a chromogenic or luminescent substrate of the enzyme can also be used. Examples of the enzyme include luciferase, peroxidase, and alkaline phosphatase. Chromogenesis can be achieved by using chromogenic materials such as luciferin, 3,3'-diaminobenzidine (DAB), 5-bromo-4-chloro-3-indolyl phosphate (BCIP) and 3,3'-(3,3'-dimethoxy-4,4'-biphenylene)bis[2-(4-nitrophenyl)-5-phenyl-2H-tetrazolium chloride] (NBT) as substrates of these enzymes in combination. As labeled substances used for detection by a nuclear magnetic resonance method, paramagnetic substances represented by gadolinium, magnetic particles represented by iron oxide microparticles and nuclear magnetic resonance-active nuclides can preferably be used. Examples of radionuclides used for detection with a γ-counter include $^{123}$I, $^{201}$Tl, $^{67}$Ga, $^{99m}$Tc, $^{111}$In and so forth. As positron-emitting nuclides, $^{15}$O, $^{13}$N, $^{11}$C, $^{18}$F and the like can be used. Furthermore, as nuclear magnetic resonance-active nuclides, $^{1}$H, $^{13}$C, $^{15}$N, $^{19}$F, $^{23}$Na, $^{29}$Si, $^{31}$P and the like can be used. When such a nuclear magnetic resonance-active nuclide is present, a phosphorylated peptide or protein can be detected by utilizing a nuclear magnetic resonance method. Specifically, a phosphorylated peptide or protein and the metal complex compound of the present invention are brought into contact with each other, and the phosphorylated peptide or protein can be detected by measuring a change in an NMR signal derived from the metal complex compound after the contact. Furthermore, imaging of a phosphorylated peptide or protein can also be performed by using the above-mentioned detection methods. Furthermore, the compound of the present invention can also be utilized as a kinase activity-detecting compound for detecting kinase activation. In this case, a change in a signal such as a luminescence signal of the compound induced by binding of the compound of the present invention to a peptide by phosphorylation of a substrate peptide by a kinase in the presence of a target kinase, a substrate peptide (substrate protein) and the compound of the present invention is observed as a kinase activity. The compound of the present invention and a peptide may also be crosslinked to the compound to a phosphate group in a phosphorylated substrate peptide or protein. Furthermore, imaging of a kinase activity can be performed by using this detection method.

Furthermore, when such a nuclear magnetic resonance-active nuclide as described above is present, a kinase activity can be detected by utilizing a nuclear magnetic resonance method. That is, along with activation of the kinase in the presence of a substrate peptide or protein, the metal complex compound of the present invention is crosslinked to a phosphate group of a phosphorylated substrate peptide or substrate protein. As a result, a change in a nuclear magnetic resonance signal of the metal complex compound is induced, and the kinase activity can be detected by measuring this change. Furthermore, imaging of a kinase activity can also be performed by using this detection method.

One of important and effective targets of the compound of the present invention is a tau protein. Tau proteins are thermostable proteins that are mainly expressed in the brain, and six isoforms are present due to selective splicing of a single gene. These proteins regulate stability and orientation of microtubules existing in nerve cells, astrocytic cells and oligodendroglia cells. The major function of tau proteins is to stabilize and bundle microtubules in the nerve axon. When an ability to bind to microtubules is lost due to abnormal phosphorylation of tau proteins, microtubules become unstable. Since microtubules form the cytoskeleton, the shape of the cell cannot be maintained, leading to nerve cell death. At this time, excessively phosphorylated tau proteins become fibrotic and accumulated (neurofibrillary tangle). Such a neurofibrillary tangle is known to be a pathological characteristic that is the most marked in the brain affected by neurodegenerative diseases represented by Alzheimer's disease. The phosphorylation sites of tau proteins in Alzheimer's disease have been identified by mass spectrometry or by using a phosphorylation dependent anti-tau antibody, and serine or threonine is phosphorylated at 25 sites on a tau protein. Furthermore, GSK3β, MAP kinase (ERK1, ERK2, p38), CDK5, JNK3, PKA, PKC, CaM kinase II and SAP kinase are known as taurine oxidases. Based on these findings, compounds that can selectively recognize phosphorylation at specific sites among phosphorylation sites of tau proteins can be used for studies and diagnoses of Alzheimer's disease based on the presence of excessively phosphorylated tau proteins. For example, efficacy of detection of Alzheimer's disease based on the detecting of phosphorylation of 231st threonine (Thr231) and 235th serine (Ser235) in a multisite phosphorylated tau protein has been reported in Koichi Ishiguro et al., Neuroscience Letters, (1999) 270, 91-94. Furthermore, the metal complex compound of the present invention can contribute to elucidation of involvement of specific phosphorylation sites in the aggregate formation, inhibition of aggregate formation and development of specific kinase inhibitors. That is, a multisite phosphorylated tau protein or peptide that can be detected by the metal complex compound of the present invention may be a partial sequence peptide, and may be a tau protein in which at least Thr231 and Ser235 are phosphorylated or a partial sequence peptide of a phosphorylated tau protein.

As an exemplary embodiment, the cerebrospinal fluid or a pathological section of the brain and the compound are brought into contact with each other, and the presence of a phosphorylated tau protein can be detected. Furthermore, the compound of the present invention can also be utilized as a compound for in-vivo imaging of excessively phosphorylated tau proteins in the brain affected by Alzheimer's disease. The presence of excessively phosphorylated tau proteins in an individual to which the compound has been administered is observed with a suitable detection system. At this time, it is desirable that the compound contains a fluorescent substance that is excited and emits light in the near-infrared region, a paramagnetic substance such as gadolinium, a magnetic particle such as iron oxide microparticles, a γ-ray-emitting nuclide or positron-emitting nuclide.

Accordingly, the present invention includes a method for detecting a phosphorylated protein or peptide or a kinase activity, preferably a luminescence detection method, including bringing the multisite phosphate group-recognizing compound of the present invention into contact with a target protein or peptide and detecting the presence of a phosphorylated protein or peptide or a kinase activity based on a change in luminescence of the compound by measurement of luminescence.

The multisite phosphate group-recognizing compound of the present invention can be used for a method for imaging a phosphorylated protein or peptide and a method for imaging a kinase activity. Therefore, the compound can be used for diagnosis of a disease that correlates with the amount of a phosphorylated protein or peptide or a kinase activity. The compound can also be used for a method for imaging abnormal phosphorylation of disease-related proteins or kinase activity and, preferably, for luminescence imaging. The luminescence imaging compound can be used for studies of diseases using cultured cells and tissues as measurement samples. Furthermore, for diagnosis of conditions of a patient with the disease or diagnosis for prophylactic treatment of a disease in a healthy subject, the compound can be introduced into an organism or cells or tissues collected from an organism and used for a method for imaging a phosphorylated protein or a kinase activity or, preferably, fluorescence imaging.

Furthermore, Alzheimer's disease can be diagnosed by detecting a phosphorylated peptide or protein using the compound of the present invention. Specifically, the compound of the present invention can be introduced into cultured cells, cells or tissues collected from an organism or an organism, along with contact between the phosphorylated peptide or protein and the compound, the compound is crosslinked to a phosphate group in the phosphorylated peptide or protein, resulting in induction of a change in a luminescence signal of the compound, and whether the patient has Alzheimer's disease or not can be determined by detecting the presence or absence of a phosphorylated peptide or protein by measuring this change, so that.

Furthermore, whether the patient has Alzheimer's disease or not can also be diagnosed by detecting a phosphorylated peptide or protein utilizing a nuclear magnetic resonance method. Specifically, Alzheimer's disease can be diagnosed by introducing the compound of the present invention into cultured cells, cells or tissues collected from an organism or an organism, bringing a phosphorylated peptide or protein and the compound of the present invention into contact with each other, measuring a change in an NMR signal derived from the metal complex compound after the contact, and detecting the presence of phosphorylated peptide or protein based on this change in the signal.

The above-mentioned method for diagnosing Alzheimer's disease may include monitoring the location and the condition of a disease such as Alzheimer's disease by detecting a disease-related phosphorylated protein (peptide) or a disease-related kinase activity.

The diagnosis method by detection of luminescence using the multisite phosphate group-recognizing compound of the present invention includes introducing the compound into cultured cells, cells or tissues collected from an organism or an organism and monitoring the location and the condition of a disease by detecting a disease-related phosphorylated protein or a disease-related kinase activity.

The present invention also relates to a kit that can be used for a study or to perform a diagnostic assay defined above. There is provided a kit for detecting or quantifying the presence of phosphorylated tau peptides or tau proteins, multisite phosphorylated peptides or proteins or measuring a kinase activity, which includes at least the compound of the present invention. Furthermore, if necessary, such a kit includes a reagent used for the measurement, for example, an antibody that recognizes a target peptide or protein. This antibody is a monoclonal antibody or a polyclonal antibody and includes an antibody labeled for detection, if necessary. Furthermore, the kit can suitably include a vessel, reagents necessary for assays, such as a buffer, a positive control reagent, a negative control reagent, a kinase inhibitor, an instruction manual and so forth. As described above, a diagnostic kit including the compound of the present invention that can detect multisite phosphorylated tau proteins or peptides involved in Alzheimer's disease provides noninvasive means that can diagnose Alzheimer's disease rapidly and economically. FIG. 1 is a schematic view illustrating the method for detecting a phosphorylated protein or peptide provided by the present invention. A phosphate group-recognizing compound (A) recognizes the distance of multisite phosphate groups (B) and binds to a phosphorylated protein or peptide (C). Since a signal (D) from compound (A), for example, fluorescence, differs in the intensity and the maximum wavelength thereof before and after the binding, the presence or absence of a phosphorylated protein or peptide can be detected by the compound.

Figure 2:
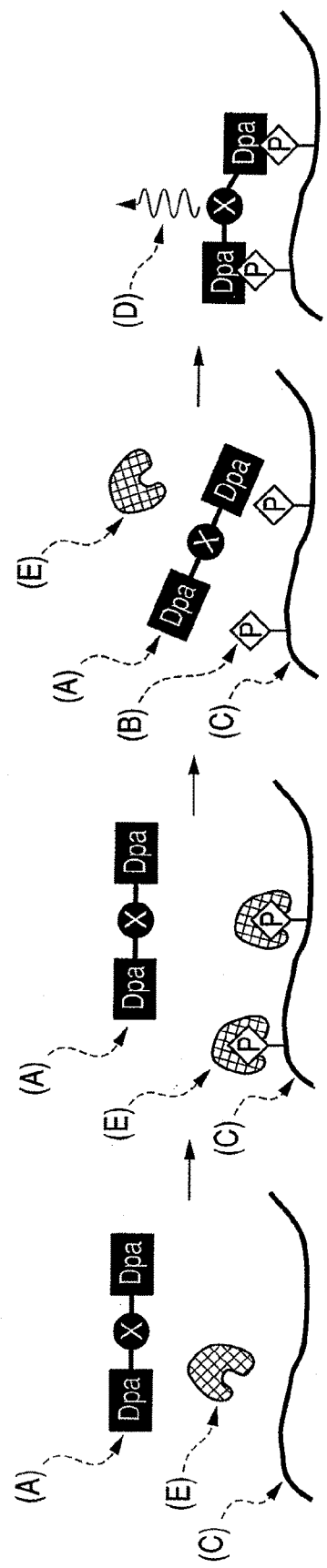
FIG. 2 is a schematic view illustrating the method for detecting a kinase activity using the multisite phosphate group-recognizing compound provided by the present invention (P represents a phosphate group, and X represents a spacer between two Dpa's).

Furthermore, when a nuclear magnetic resonance (NMR) signal is utilized, a phosphate group-recognizing compound (A) having a nuclear magnetic resonance-active nuclide recognizes the distance between multisite phosphate groups (B) and binds to a phosphorylated protein or peptide (C). The presence or absence of a phosphorylated protein or peptide can be detected by the compound by observing a nuclear magnetic resonance signal (NMR signal) (D) from compound (A) or observing a change in the signal intensity or a chemical shift after the binding. FIG. 2 is a schematic view illustrating the method for detecting a kinase activity provided by the present invention. When phosphorylation by a kinase (E) occurs at multiple sites, the phosphate group-recognizing compound (A) that is allowed to coexist recognizes the distance between the phosphate groups (B) and binds to a phosphorylated protein or peptide (C). Since a signal (D) from compound (A), for example, fluorescence, differs in the intensity and the maximum wavelength thereof before and after the binding, a kinase activity can be detected by detecting the presence or absence of a phosphorylated protein or peptide by the compound.

Furthermore, when a nuclear magnetic resonance (NMR) signal is used, phosphorylation by a kinase (E) occurs at multiple sites, a phosphate group-recognizing compound (A) having a nuclear magnetic resonance-active nuclide that coexists recognizes the distance between the phosphate groups (B) and binds to a phosphorylated protein or peptide (C). A kinase activity can be detected by detecting the presence or absence of a phosphorylated protein or peptide by the compound by observing a magnetic resonance signal (D) from compound (A) or observing a change in the signal intensity or a chemical shift after the binding.

EXAMPLES

Hereafter, the present invention will be described with reference to the following examples to further clarify characteristics of the present invention. However, the scope of the present invention is not limited to these examples. In the present specification and the chemical structural formulas in the accompanying drawings, carbon atoms and hydrogen atoms may be omitted according to the conventional rules. In the chemical structural formulas, a coordinate bond is expressed with a broken line.

Example 1

Synthesis of Luminescent Compound

Figure 3:
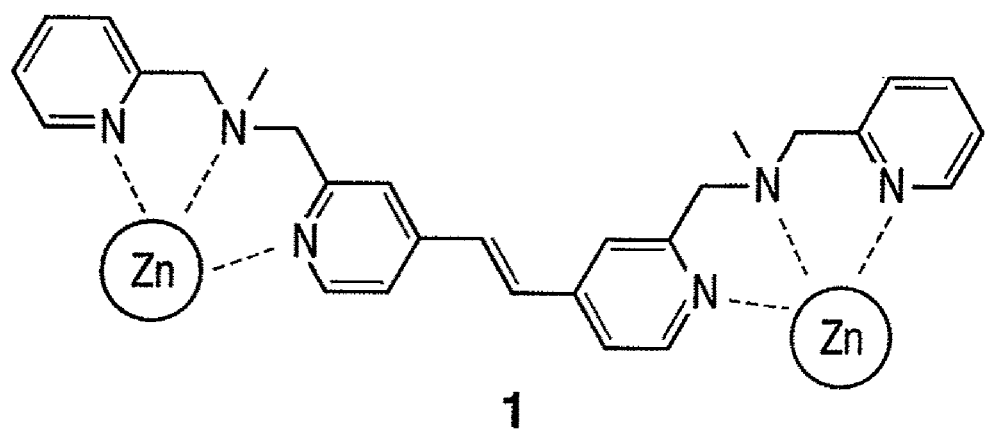
FIG. 3 illustrates a structural formula of a synthesized Zn(Dpa)-stilbazole complex compound 1.
Figure 4:
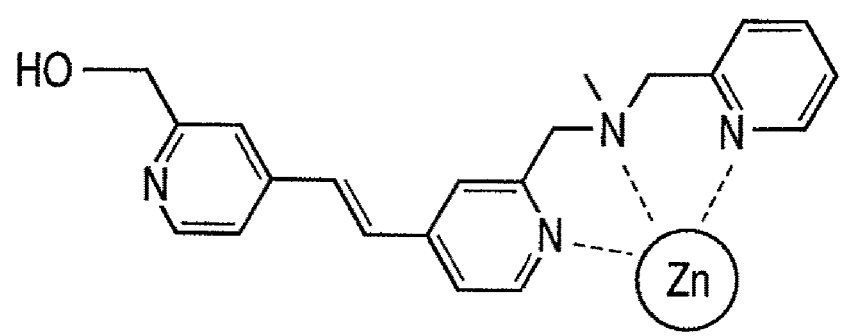
FIG. 4 illustrates a structural formula of a synthesized mononuclear Dpa compound 2.
Figure 5:
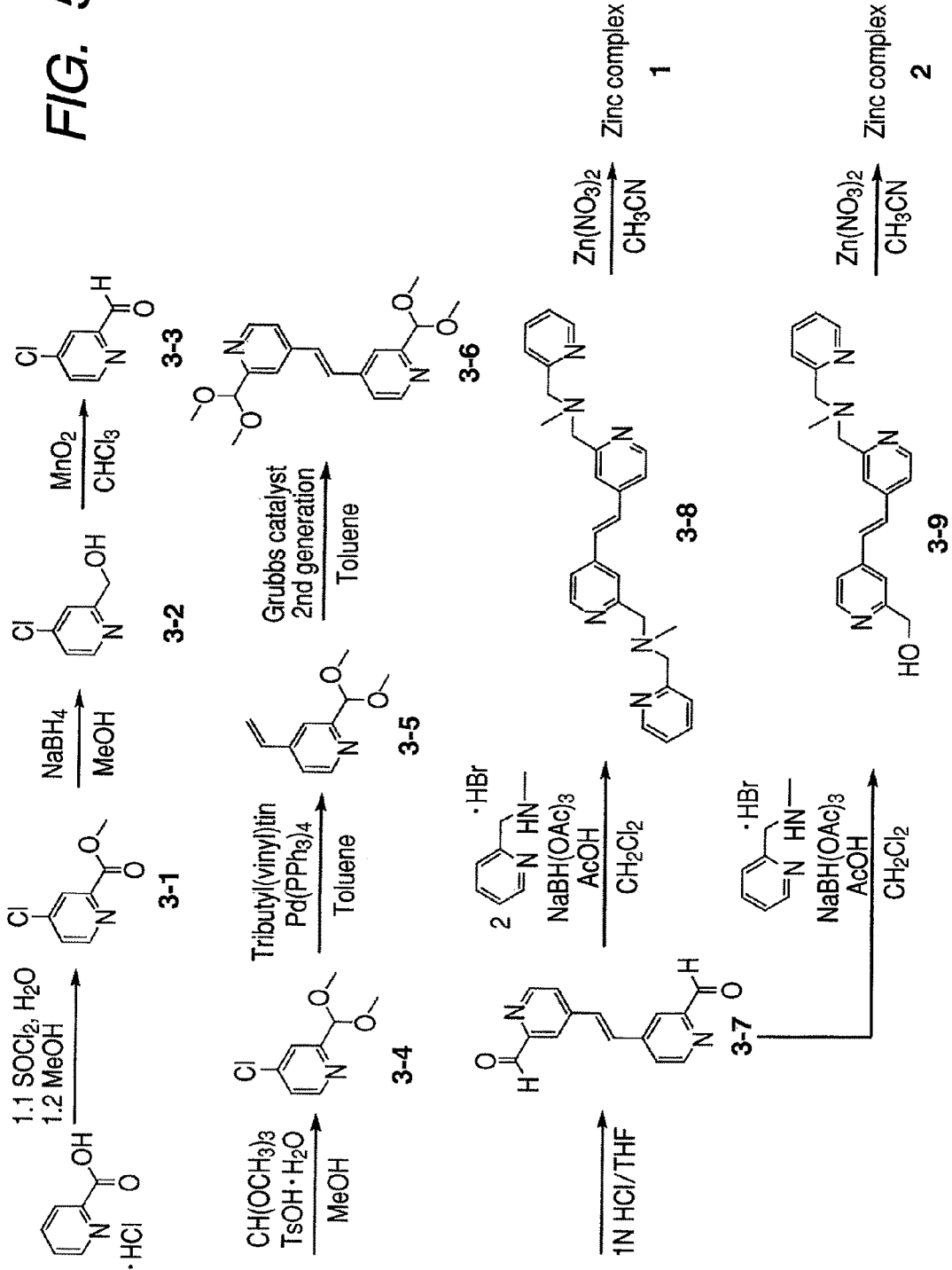
FIG. 5 illustrates a synthesis scheme of the Zn(Dpa)-stilbazole complex 1 and the mononuclear Dpa compound 2.

As the luminescent compound of the present invention, a Zn(Dpa)-stilbazole complex 1 (FIG. 3) represented by the above-mentioned formula (16) was synthesized by the following scheme. For comparison, a compound 2 having one Dpa (FIG. 4) was also synthesized. FIG. 5 illustrates a synthesis scheme.

Example 1(1)

Synthesis of Compound 3-1

5.0 g (31.7 mmol) of 2-pyridinecarboxylic acid hydrochloride and 15 mL of thionyl chloride were placed in a 100-mL three-neck recovery flask and stirred on an ice bath. 0.5 mL (31.7 mmol/1 eq) of distilled water was slowly added dropwise to this mixture solution, and then reflux with heating was started. The reaction was followed by TLC (hexane/EtOAc=1/1), and completion of the reaction was confirmed three days later. The solvent was evaporated under reduced pressure, toluene was further added, and the mixture was evaporated under reduced pressure. When 30 mL of toluene was added to the residue, the mixture was cooled on an ice bath, MeOH (1.3 eq) was slowly added dropwise, and solids were precipitated. The precipitated solids were isolated by filtration and washed with toluene. The resulting solids were dissolved in chloroform and washed with aqueous saturated sodium hydrogencarbonate. The organic layer was dried with magnesium sulfate, and then the solvent was evaporated under reduced pressure. Purification was performed by column chromatography (silica gel, hexane/EtOAc=3/1) to obtain 2.52 g (46.3%) of a white solid. Identification was performed by $^1$H-NMR and FAB-MS. ($^1$H-NMR (400 MHz, CDCl$_3$, 25° C., TMS) δ/ppm; 4.02 (3H, s), 7.49 (1H, dd, J=2.0, 4.8 Hz), 8.14 (1H, ds J=2.0 Hz), 8.65 (1H, d, J=4.8 Hz). FAB-LRMS m/e 172 [M+H]$^+$.)

Example 1(2)

Synthesis of Compound 3-2

1.5 g (8.74 mmol) of compound 3-1, 5 mL of THF and 10 mL of MeOH were placed in a 50-mL two-neck recovery flask, and the mixture was stirred on an ice bath. 3.8 g (4.0 eq) of CaCl$_2$ and 658 mg (2.0 eq) of NaBH$_4$ were added to the mixture solution, and the mixture was stirred continuously. The reaction was followed by TLC (hexane/EtOAc=1/1), and completion of the reaction was confirmed 1 h later. Ethyl acetate was added to the reaction solution, and the mixture was extracted with ethyl acetate. The organic layer was dried with magnesium sulfate, and then the solvent was evaporated under reduced pressure to obtain 1.23 g (quant.) of a colorless oily compound. Identification was performed by $^1$H-NMR and FAB-MS. ($^1$H-NMR (400 MHz, CDCl$_3$, 25° C., TMS) δ/ppm; 4.75 (s, 2H), 7.22 (d, 1H, J=5.2 Hz), 7.31 (s, 1H), 8.45 (d, 1H, J=5.2 Hz). FAB-LRMS m/e 144 [M+H]$^+$)

Example 1(3)

Synthesis of Compound 3-3

1.23 g (8.56 mmol) of compound 3-2, 15 mL of chloroform and 9.2 g (7.5 times (by weight) S.M.) of manganese dioxide were placed in a 100-mL two-neck recovery flask, and the mixture was heated to reflux. The reaction was followed by TLC (hexane/EtOAc=1/1), and completion of the reaction was confirmed 2 h later. Insoluble matters were removed by Celite filtration, and the filtrate was evaporated under reduced pressure to obtain 1.20 g (quant.) of a pale yellow oily compound. Identification was performed by $^1$H-NMR and CI-MS. ($^1$H-NMR (400 MHz, CDCl$_3$, 25° C., TMS) δ/ppm; 7.52 (dd, 1H, J=2.0, 5.2 Hz), 7.95 (ds, 1H, J=2.0 Hz), 8.68 (d, 1H, J=5.2 Hz), 10.1 (s, 1H). CI-MS m/e 140 [M−H]$^+$

Example 1(4)

Synthesis of Compound 3-4

600 mg (4.24 mmol) of compound 3-3, 15 mL of methanol, 0.71 mL (2.1 eq) of trimethyl ortho-formate and 32.2 mg (0.04 eq) of p-toluenesulfonic acid monohydrate were placed in a 50-mL two-neck recovery flask, and the mixture was heated to reflux. The reaction was followed by TLC (hexane/EtOAc=1/1), and completion of the reaction was confirmed 5 h later. The solvent was evaporated under reduced pressure, followed by addition of ethyl acetate, and the mixture was washed with 2 N aqueous sodium hydroxide. The organic layer was dried with magnesium sulfate, and the solvent was evaporated under reduced pressure to obtain 571.2 mg (80.1%) of a pale yellow oily compound. Identification was performed by $^1$H-NMR and FAB-MS. ($^1$H-NMR (400 MHz, CDCl$_3$, 25° C., TMS) δ/ppm; 3.41 (s, 6H), 5.36 (s, 1H), 7.27 (dd, 1H, J=2.0, 5.2 Hz), 7.58 (ds, 1H, J=2.0 Hz), 8.51 (d, 1H, J=5.2 Hz). FAB-LRMS m/e 188 [M+H]$^+$)

Example 1(5)

Synthesis of Compound 3-5

571.2 mg (3.04 mmol) of compound 3-4, 20 mL of dry toluene, 1.1 mL (1.2 eq) of tributylvinyl tin and 350 mg (10% by mole of S.M.) of Pd(PPh$_3$)$_4$ were placed in a 100-mL two-neck recovery flask deaerated by argon substitution, and the mixture was heated to reflux. The reaction was followed by TLC (hexane/EtOAc=1/1), and completion of the reaction was confirmed one day later. Insoluble matters were isolated by Celite filtration, and the filtrate was evaporated under reduced pressure. Diisopropyl ether was added, precipitated insoluble matters were isolated by filtration, and the filtrate was evaporated under reduced pressure. Purification was performed by column chromatography (silica gel, hexane/EtOAc=3/1) to obtain 446.8 mg (82.0%) of a yellow oily compound. Identification was performed by $^1$H-NMR and FAB-MS. ($^1$H-NMR (400 MHz, CDCl$_3$, 25° C., TMS) δ/ppm; 3.42 (s, 6H), 5.37 (s, 1H), 5.50 (d, 1H, J=10.8 Hz), 6.00 (d, 1H, J=17.6 Hz), 6.68 (dd, 1H, J=10.8, 17.8 Hz), 7.23 (dd, 1H, J=1.6, 5.2 Hz), 7.53 (s, 1H), 8.56 (d, 1H, J=4.8 Hz). FAB-LRMS m/e 180 [M+H]$^+$.)

Example 1(6)

Synthesis of Compound 3-6

308.9 mg (1.72 mmol) of compound 3-5, 15 mL of dry toluene and 57 mg (2nd generation, 5% by mole) of Grubbs' catalyst were placed in a 50-mL two-neck recovery flask, and the mixture was heated to reflux. The reaction was followed by TLC (hexane/EtOAc=1/5), and completion of the reaction was confirmed one day later. Insoluble matters were isolated by Celite filtration, and the filtrate was evaporated under reduced pressure. Diisopropyl ether was added, precipitated insoluble matters were isolated by filtration, and the filtrate was evaporated under reduced pressure. Then, hexane was added, and precipitated insoluble matters were isolated by filtration. When the filtrate was evaporated under reduced pressure, solids were precipitated. Solid-liquid wash was performed with a mixed solvent of hexane/diisopropyl ether (1:1), and the resulting solid was dried under reduced pressure to obtain 109.4 mg (38.2%) of a pale brown solid. Identification was performed by $^1$H-NMR and FAB-MS. ($^1$H-NMR (400 MHz, CDCl$_3$, 25° C., TMS) δ/ppm; 3.44 (s, 12H), 5.41 (s, 2H), 7.28 (s, 2H), 7.34 (dd, 2H, J=2.0, 5.2 Hz), 7.68 (s, 2H), 8.62 (d, 2H, J=2.0, 5.2 Hz). FAB-LRMS m/e 331 [M+H]$^+$.)

Example 1(7)

Synthesis of Compound 3-7

50 mg (0.15 mmol) of compound 3-6, 7 mL of THF and 3 mL of 1 N aqueous HCl solution were placed in a 25-mL two-neck recovery flask, and the mixture was stirred at room temperature. The reaction was followed by TLC (hexane/EtOAc=1/5). However, since disappearance of the raw material was not confirmed, 1 mL of concentrated hydrochloric acid was added, and the mixture was stirred at 50° C. Heating was started, and disappearance of the raw material was confirmed by TLC 4 h later. Therefore, the mixture solution was neutralized with aqueous saturated sodium hydrogencarbonate and extracted with ethyl acetate. The organic layer was washed with saturated brine and dried with magnesium sulfate, and the solvent was evaporated under reduced pressure to obtain 46.8 mg (quant.) of a pale brown oily compound. Identification was performed by $^1$H-NMR and FAB-MS. ($^1$H-NMR (400 MHz, CDCl$_3$, 25° C., TMS) δ/ppm; 7.39 (s, 2H), 7.61 (dd, 2H, J=2.0, 5.2 Hz), 8.11 (s, 2H), 8.83 (d, 2H, J=5.2 Hz), 10.1 (s, 2H). FAB-LRMS m/e 239 [M+H]$^+$.)

Example 1(8)

Synthesis of Compound 3-8

35.7 mg (0.15 mmol) of compound 3-7, 15 mL of dichloroethane, one drop of acetic acid, 67.0 mg (HBr salt, 2.2 eq) of picolylamine, and 150 mg (4.0 eq) of Na(OAc)$_3$BH were placed in a 100-mL of two-neck recovery flask, and the mixture was stirred at room temperature. The reaction was followed by TLC(CHCl$_3$/MeOH=10/1, containing aqueous NH$_3$), and completion of the reaction was confirmed 7 h later. Aqueous saturated sodium hydrogencarbonate was added to the reaction solution to neutralize the solution, and the mixture was extracted with chloroform. The organic layer was washed with saturated brine and dried with magnesium sulfate, and the solvent was evaporated under reduced pressure. Purification was performed by column chromatography (silica gel, CHCl$_3$/MeOH=40/1→20/1, containing aqueous NH$_3$) to obtain 446.8 mg (82.0%) of a yellow oily compound. Identification was performed by $^1$H-NMR and FAB-MS. ($^1$H-NMR (400 MHz, CD$_3$OD, 25° C., TMS) δ/ppm; 2.30 (s, 6H), 3.78 (s, 8H), 7.30 (t, 2H, J=4.8 Hz), 7.51 (s, 2H), 7.54 (d, 2H, J=2.0, 5.2 Hz), 7.65 (d, 2H, J=8.0 Hz), 7.80-7.84 (m, 4H), 8.46-8.49 (m, 4H). FAB-LRMS m/e 451 [M+H]$^+$)

Example 1(9)

Synthesis of Compounds 3-9

Compounds 3-9 was synthesized in the same manner as in the synthesis of compound 3-8, except that 1 equivalent of picolylamine was added, and a solution of picolylamine in dichloroethane was slowly added dropwise on an ice bath. Further, the major product was one of two aldehydes oxidized to benzyl alcohol with Na(OAc)$_3$BH during the reaction. Using compound 3-7 as the starting material (35.7 mg [0.15 mmol]), 35.1 mg (67.3%) of a yellow oily compound was obtained. Identification was performed by $^1$H-NMR and FAB-MS. ($^1$H-NMR (400 MHz, CD$_3$OD, 25° C., TMS) δ/ppm; 2.36 (s, 3H), 3.80 (s, 4H), 4.80 (s, 2H), 7.17 (t, 1H, J=4.4 Hz), 7.31 (d, 1H, J=5.2 Hz), 7.37 (s, 1H), 7.49 (d, 1H, J=7.6 Hz), 7.65-7.69 (m, 2H), 8.55-8.59 (3H). FAB-LRMS m/e 347 [M+H]$^+$)

Example 1(10)

Synthesis of Compound 1

42.9 mg (0.095 mmol) of compound 3-8, 10 mL of acetonitrile and 591.2 μL (1.9 eq) of 305.99 mM aqueous Zn(NO$_3$)$_2$ were placed in a 50-mL one-neck recovery flask, and the mixture was stirred at room temperature. Since solids were precipitated in the reaction solution 2 h later, the solids were isolated by filtration and washed with acetonitrile, and then the resulting solids were dried under reduced pressure to obtain 49.1 mg (62.1%) of a white solid. Identification was performed by $^1$H-NMR, FAB-MS and elemental analysis. ($^1$H-NMR (400 MHz, D$_2$O, 25° C., TMS) δ/ppm; 2.27 (s, 6H), 4.03-4.17 (m, 8H), 7.45-7.52 (m, 6H), 7.63-7.67 (m, 4H), 7.96 (t, 2H, J=7.6 Hz), 8.51-8.53 (m, 4H). FAB-LRMS m/e 768 [M-NO$_3$$^-$+H]$^+$. Anal Calcd for C$_{28}$H$_{30}$N$_6$.2Zn(NO$_3$)$_2$: C, 40.55; H, 3.65; N, 16.89. Found: C, 40.71; H, 3.65; N, 17.02.)

Example 1(11)

Synthesis of Compound 2

Compound 2 was synthesized in the same manner as in the synthesis of compound 1. Although 1 eq of aqueous Zn(NO$_3$)$_2$ was added, and the mixture was stirred, no solid was precipitated. Therefore, the solvent was evaporated under reduced pressure, and precipitation of solids was confirmed. Solid-liquid wash was performed for the precipitated solids with acetonitrile, and the resulting solids were dried under reduced pressure. Using compound 3-9 as the starting material (20.0 mg [0.058 mmol]), 7.0 mg (22.5%) of a yellow oily compound was obtained. Identification was performed by $^1$H-NMR and FAB-HRMS. ($^1$H-NMR (400 MHz, D$_2$O, 25° C., TMS) δ/ppm; 2.26 (s, 3H), 4.04-4.16 (m, 4H), 7.39-7.52 (m, 5H), 7.59-7.66 (m, 3H), 7.97 (t, 1H, J=7.6 Hz), 8.39 (d, 1H, J=5.2 Hz), 8.49 (d, 1H, J=5.2 Hz), 8.53 (d, 1H, J=4.8 Hz). Benzyl proton overlaps the D$_2$O peak. FAB-HRMS m/e 472.0963 [M-NO$_3$$^-$+H]$^+$)

Example 1(12)

Designing of Target Multisite Phosphorylated Peptides

Partial sequence of a tau protein phosphorylated particularly at the positions of (i, i+2) among phosphorylation sites were used to design and synthesize the target peptides. Furthermore, tau sequence peptides having two phosphate groups at the positions of (i, i+4) or (i, i+6) were also synthesized as control peptides. Furthermore, to determine whether the compound molecule of the present invention can recognize only specific phosphorylation sites, a triphosphate peptide phosphorylated at the positions of (i, i+4, i+6) (Tau$_{204-216}$3P) was synthesized at the same time. FIG. 6 lists the synthesized phosphorylated peptides.

Example 1(13)

Synthesis of Multisite Phosphorylated Peptides

All the peptides were synthesized with an automated peptide synthesizer (ABI 433A, Applied Biosystems). Standard Fmoc-based FastMoc Coupling Chemistry was used as a software. Fmoc-protected amino acids and reagents used for peptide synthesis were purchased from Watanabe Chemical Industries, Ltd. 4 equivalents of Fmoc amino acids (0.4 mmol) based on the amide resin (introduction rate, 0.64 mmol/g, 0.1 mmol scale) was placed in a vial for synthesis and subjected to automatic synthesis (synthesis included the deprotection of the N terminal amino acid). Excision from the resin and deprotection were performed according to the following procedure. The obtained resin was placed in a 50-mL recovery flask, required amounts of reagents for excision and deprotection (0.06 mL of m-cresol, 0.36 mL of thioanisole and 2.58 mL of trifluoroacetic acid based on 300 mg of the resin) were added, and the mixture was stirred at room temperature for 1 h. The resin was isolated by filtration, and the filtrate was evaporated under reduced pressure. TBME was added, and precipitates of a produced crude peptide were isolated by filtration and dried under reduced pressure in a desiccator. The resulting crude peptide was dissolved in distilled water, and insoluble matters obtained after filtration by a membrane filter were purified by HPLC (column, ODS-A [YMC Co., Ltd., 10 mm×250 mm, 30 mm]; mobile phase, A/B=5/95 to 40/60; gradient over 40 min. A, acetonitrile (0.1% TFA); B, distilled water (0.1% TFA); flow rate, 3 mL/min; detection wavelength, 220 nm). Identification was performed by MALDI-TOF MS (Tau$_{210-220}$2P: calculated value ([M−H]$^-$), 1512.61; measured value, 1506.83) (Tau$_{231-238}$2P: calculated value ([M−H]$^-$), 1117.39; measured value, 1111.81) (Tau$_{227-238}$2P: calculated value ([M−H]$^-$), 1542.47; measured value, 1552.0) (Tau$_{204-216}$3P: calculated value ([M−H]$^-$), 1808.47; measured value, 1813.8) (Tau$_{204-216}$2P (i, i+4): calculated value ([M−H]$^-$), 1730.72; measured value, 1722.75) (Tau$_{204-216}$2P (i, i+6): calculated value ([M−H]$^-$), 1730.72; measured value, 1733.9). The peptide solution was divided and lyophilized.

Example 1(14)

Evaluation of Peptide Recognizing Abilities of Compounds 1 and 2

(Examination Using Tau$_{210-220}$2P)
The peptide recognizing abilities of compounds 1 and 2 were evaluated by measuring fluorescence spectra. Measurement was performed under conditions of [compound 1 or 2=10 µM, an optical path length of 1 cm, pH 7.2, 50 mM HEPES buffer and 25° C. The excitation wavelength was λex=323 nm, Ex/Em=15 nm/10 nm, except λex=323 nm, Ex/Em=5 nm/10 nm for only $Tau_{210-220}2P$, for compound 1, and λex=305 nm, Ex/Em=10 nm/12 nm for compound 2. As shown in FIG. 7, when $Tau_{210-220}2P$ was added to compound 1, the fluorescence intensity at 350 nm decreased, and the fluorescence intensity at around 430 nm on the long wavelength side increased. When the peptide was excessively added, this change reached saturation. The association constants calculated from the fluorescence changes were in the order of approx. $10^5$ $M^{-1}$. In contrast, when $Tau_{210-220}2P$ was added dropwise to compound 2, overall fluorescence only gradually decreased as shown in FIG. 8A. The above results suggested that the dual wavelength fluorescence changes in compound 1 occurred because two zinc complexes in compound 1 recognized two phosphate groups on the peptide. When the fluorescence spectra of compounds 1 and 2 themselves were compared, compound 2 emitted much weaker fluorescence on the short wavelength side and stronger fluorescence on the long wavelength side than compound 1 (FIG. 8B) ([compound 1 or 2=10 µM, λex=305 nm, Ex/Em=10 nm/12 nm, 50 mM HEPES buffer, 1 cm cell, 25° C.). These results revealed that the dual wavelength fluorescence changes in compound 1 associated with the addition of the peptide was not caused by inhibition of rotation of the stilbazole skeleton, which was initially expected, but a change in the coordination state of zinc ion of pyridine linked to a spacer (vinyl group) along with the binding to phosphate groups on the peptide.

(Examination Using Other Peptides and Phenyl Phosphate)

Figure 10A:
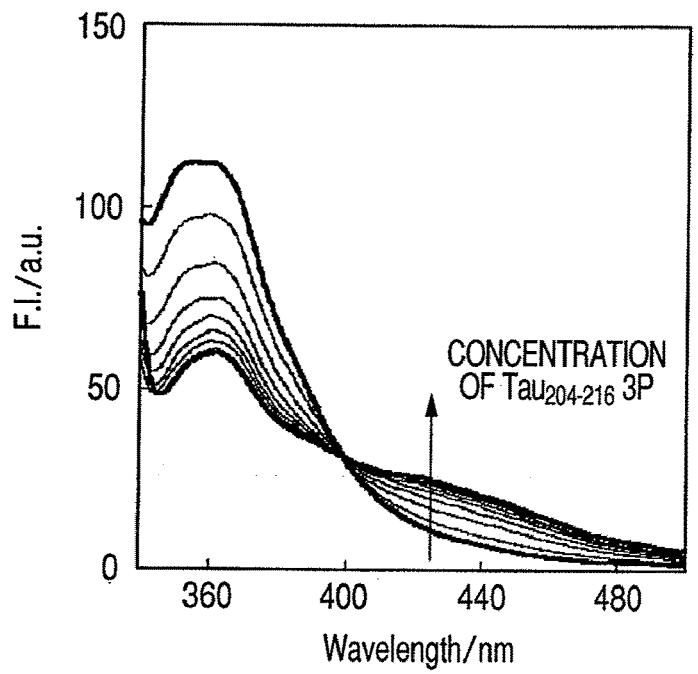
FIG. 10A illustrates changes in fluorescence of compound 1 (10 μM) with dropwise addition of $Tau_{204-216}3P$.
Figure 10B:
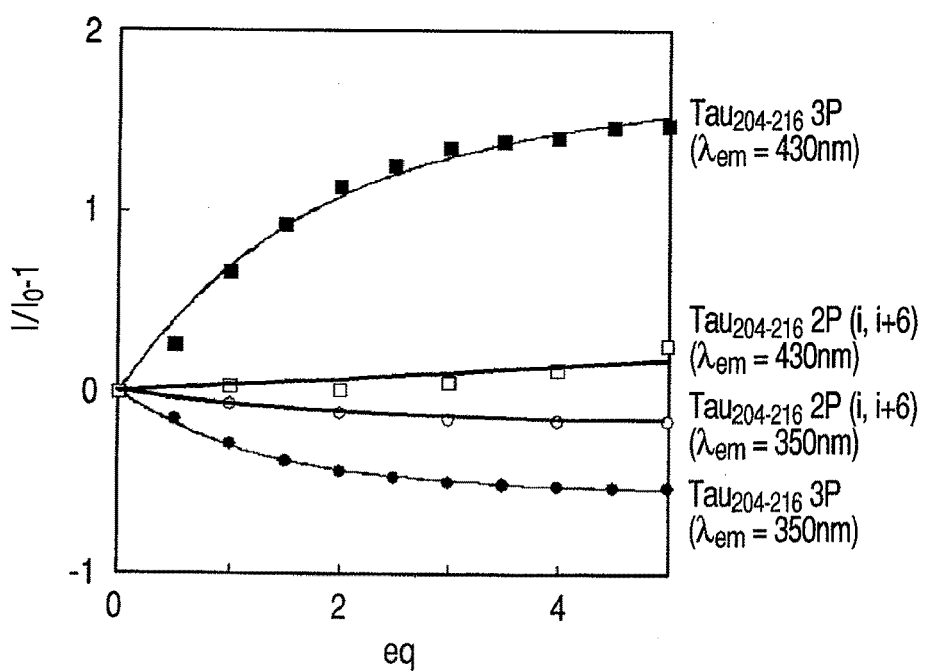
FIG. 10B illustrates a titration plot at each wavelength ($Tau_{204-216}3P$ [$\lambda_{em}$=350 nm, closed circle], $Tau_{204-216}3P$ [$\lambda_{em}$=430 nm, closed square], $Tau_{204-216}2P$ [i, i+6] [$\lambda_{em}$=350 nm, open circle], $Tau_{204-216}2P$ [i, i+6] [$\lambda_{em}$=430 nm, open square]).

FIG. 9 shows the combined multiplier at each wavelength when each peptide was added dropwise to compound 1. When peptides with two phosphate groups positioned with a distance of (i, i+2) was added dropwise, all the peptides showed dual wavelength fluorescence changes. Furthermore, all the binding constants to the peptides calculated from the fluorescence changes showed values in the order of approx. $10^5$. On the other hand, peptides with two phosphate groups with a distance of (i, i+4) or (i, i+6) did not show marked fluorescence changes. Furthermore, no marked fluorescence change was observed with phenyl phosphate, a small-molecule phosphate species, either. Among these results, it is particularly remarkable that dual wavelength fluorescence changes occurred in $Tau_{204-216}3P$, but no marked fluorescence change occurred in $Tau_{204-216}2P$ (i, i+4) or $Tau_{204-216}2P$ (i, i+6) (FIGS. 9 and 10). These results revealed that compound 1 selectively recognized phosphorylation at (i, i+2) on the peptide. Furthermore, it was also found that, when a plurality of phosphate groups exist on the same sequence, the compound bound specifically to phosphate groups at specific positions.

Example 1(15)

Examination of Affinity of Compound 1 for Tau Sequence Peptide

Figures 11, 12:
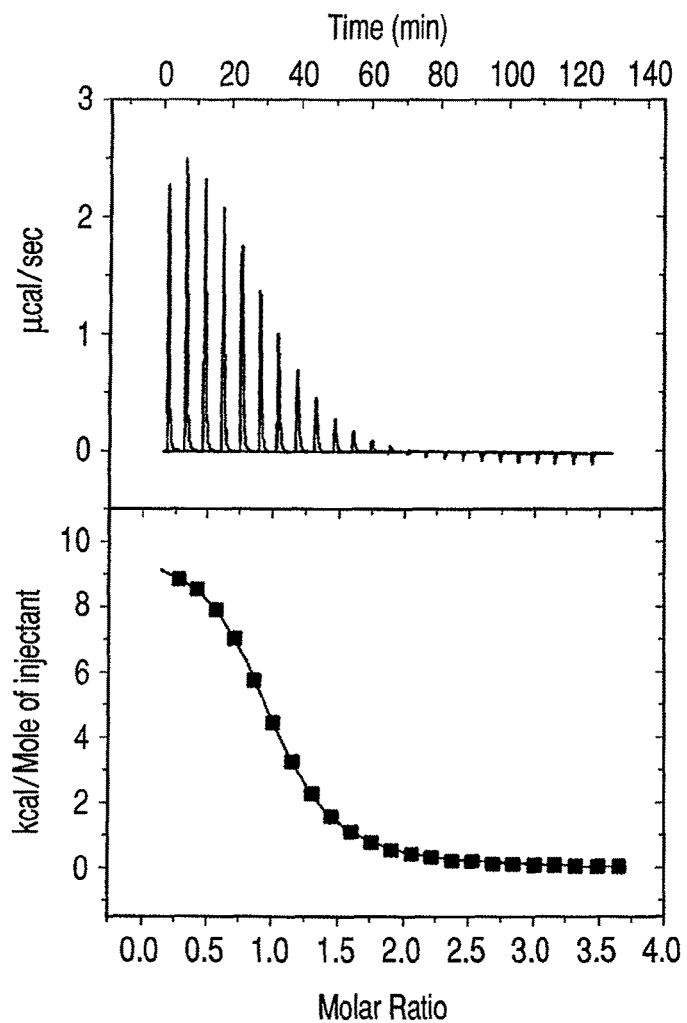
FIG. 11 illustrates changes in the amount of heat after $Tau_{210-220}2P$ was added to compound 1.
FIG. 12 is a table showing stoichiometry (N), association constant (K, $M^{-1}$), enthalpy ($\Delta H$, kcal $mol^{-1}$) and entropy ($T\Delta S$, kcal $mol^{-1}$) of compound 1 and each peptide ($Tau_{210-220}2P$, $Tau_{204-216}3P$, $Tau_{204-216}2P$ [i, i+6]) calculated from the isothermal titration calorimetry (ITC) measurement.

The above examination showed that, when a tau sequence peptide with phosphate groups at the positions of (i, i+2) was added to compound 1, dual wavelength fluorescence changes occurred. To determine whether these fluorescence changes are associated with binding, affinity was examined by ITC measurement using, in particular, three peptides of $Tau_{210-220}2P$, $Tau_{204-216}3P$ and $Tau_{204-216}2P(i, i+6)$. ITC measurement was performed under the following conditions: $Tau_{210-220}2P$, [compound 1]=100 µM and [peptide]=2 mM; $Tau_{204-216}3P$, [compound 1]=50 µM and [peptide]=1 mM; $Tau_{204-216}2P(i, i+6)$, [compound 1]=100 µM and [peptide]=3.24 mM; the number of titrations, 24; measurement temperature, 25° C.; pH 7.2; and 50 mM HEPES buffer. FIG. 11 illustrates caloric changes when $Tau_{210-220}2P$ was added to compound 1. FIG. 12 illustrates various thermodynamic parameters obtained from the caloric changes in the three different peptides. The caloric changes associated with the dropping of the peptide was an entropy-driven endothermic process ($\Delta S>0$, $\Delta H>0$). This change can be attributed to dehydration of water molecules hydrated to the compound molecules and the phosphorylated peptides along with the binding. The association constants obtained in $Tau_{210-220}2P$ and $Tau_{204-216}3P$ (K=3.33×$10^5$ $M^{-1}$ and K=2.88×$10^5$ $M^{-1}$, respectively) were similar to the values calculated from the fluorescence changes. These results suggest that the fluorescence changes when $Tau_{210-220}2P$ or $Tau_{204-216}3P$ is added to compound 1 reflect the binding. On the other hand, N=0.51 was obtained in $Tau_{204-216}2P(i, i+6)$, and it appears that two compound molecules individually interact with two phosphate groups on the peptide. Furthermore, the finding that the calculated Ka was similar to that of the mono Zn/Dpa complex also suggests that not a crosslinking structure, but an interaction in a ratio of 1:2 is present. The above results revealed that compound 1 selectively recognized and is crosslinked to two phosphate groups present at the positions of (i, i+2) on $Tau_{210-220}2P$ or $Tau_{204-216}3P$.

Example 1(16)

Verification of Mode of Binding of Compound 1 to $Tau_{210-220}2P$

Figure 13A:
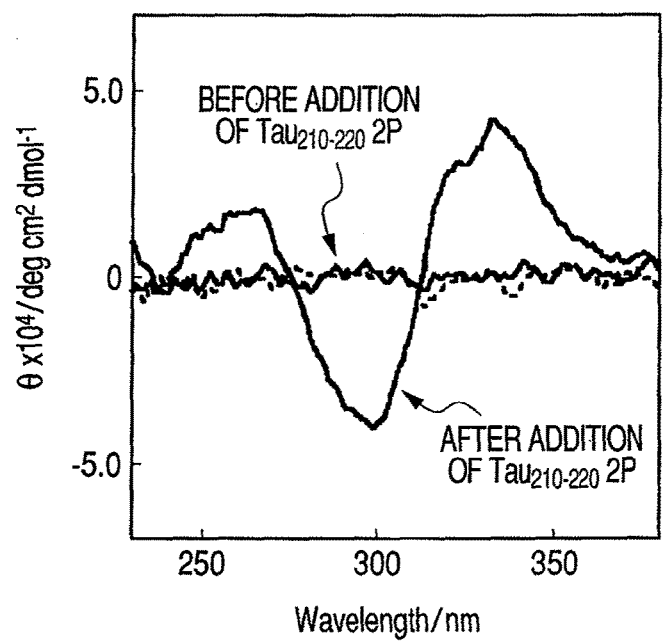
FIG. 13A illustrates changes in the CD spectrum after $Tau_{210-220}2P$ was added.

To examine the mode of interaction of compound 1 with $Tau_{210-220}2P$, a CD spectrum change after addition of a peptide to a compound molecule was measured. CD spectra were measured under the following condition: [compound 1]=20 µM; [$Tau_{210-220}2P$]=0 or 20 µM; pH 8.0; borate buffer; 2-mm cell; room temperature; the scan speed, 200 nm/min; the number of integrations, 10; response, 2 sec; and the band width, 1.0 nm. Assuming the maximum absorption wavelength of the compound molecule as 0 when $Tau_{210-220}2P$ was added to compound 1, positive and negative cotton peaks were observed (FIG. 13A). These results suggest that the compound molecule is crosslinked to two phosphate groups on $Tau_{210-220}2P$, reflecting asymmetry of the peptide in the compound. Then, utilizing the CD spectrum change (λ=291 nm) associated with the addition of $Tau_{210-220}2P$ to compound 1, a Job's plot was prepared to determine the stoichiometric ratio. To prepare the Job's plot, measurement was performed under the following conditions: [compound 1]+[$Tau_{210-220}2P$]=20 µM; pH 7.2; HEPES buffer; 1-cm cell; room temperature; the scan speed, 200 nm/min; the number of integrations, 10; response, 2 sec; and the band width, 1.0 nm. A plot which shows the maximum value with

Figure 13B:
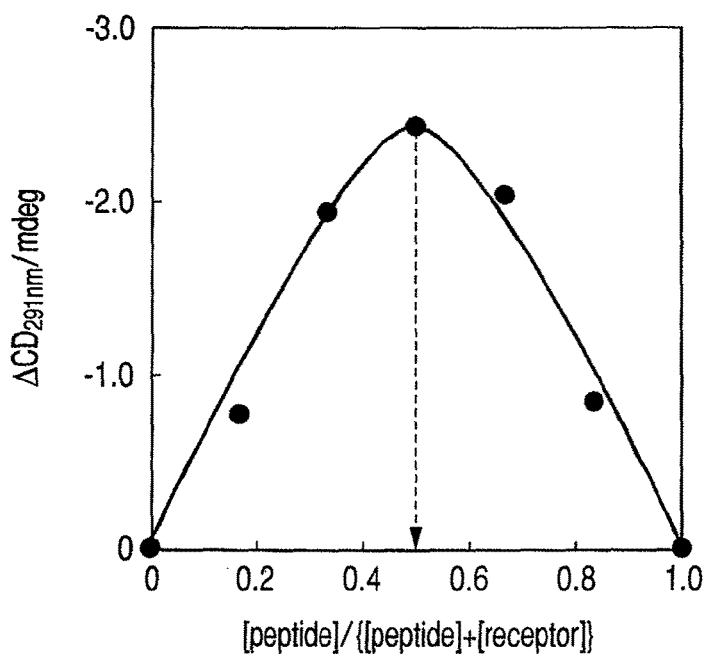
FIG. 13B illustrates Job's Plot in combination of $Tau_{210-220}2P$ and compound 1.

[Tau$_{210-220}$2P][compound]=1:1 was obtained (FIG. 13B), demonstrating that Tau$_{210-220}$2P and compound 1 bind in a ratio of 1:1. The above examination revealed that compound 1 recognizes and is crosslinked to two phosphate groups on Tau$_{210-220}$2P in a ratio of 1:1.

Example 1(17)

Conclusion

In summary, to make the skeleton of a compound molecule itself rigid, a Zn/Dpa complex was allowed to bind directly to a spacer (vinyl group), and a novel stilbazole compound in which the spacer was directly introduced at the fourth position of a pyridine ring in the Dpa was synthesized (compounds 1 and 2). Compound 1 recognizes and is crosslinked to phosphate groups existing distantly at the positions of (i, i+2) on the multisite phosphorylation sequence of a tau protein and binds in ratio of 1:1, and phosphorylation was successfully identified with dual wavelength fluorescence changes (Ka=~$10^5$ M$^{-1}$). Furthermore, it was found that compound 1 did not bind to two phosphate groups existing at the positions of (i, i+4) or (i, i+6) among a plurality of phosphate groups that existed and selectively recognized only two phosphate groups at the positions of (i, i+2). In a multisite phosphorylated peptide-recognizing compound in which a spacer binds to a nitrogen atom in a zinc complex moiety, which has already been reported (refer to Akio Ojida et al., J. Am. Chem. Soc., (2003) 125, 10184-10185), the property of recognizing the phosphate group distance is shown with about three times difference in affinity. That is, the compound interacts, although weakly, with a plurality of diphosphorylated peptides with different distances between phosphate groups. Since the used substrate peptide sequence is different from the sequence of this example, a direct comparison cannot be made, but it can be said using a fluorescence intensity change as an indicator that the compound 1 of the present invention has an improved property of recognizing the distance between diphosphoric acids.

The dual wavelength mechanism of fluorescence associated with the binding to the peptide was examined. As a result, the mechanism was found to be derived from a change in coordination of zinc ion into pyridine in the spacer associated with coordination to phosphate groups on the peptide. Since this compound can recognize only a specific phosphorylation sequence on a tau protein, the compound can be used for detection or isolation of tau proteins, further, development of inhibitors of specific tau kinases, elucidation of aggregate formation of specific tau kinases and so forth.

Example 2

Synthesis of Luminescent Compound (BODIPY-Zn(Dpa))

Figure 14:
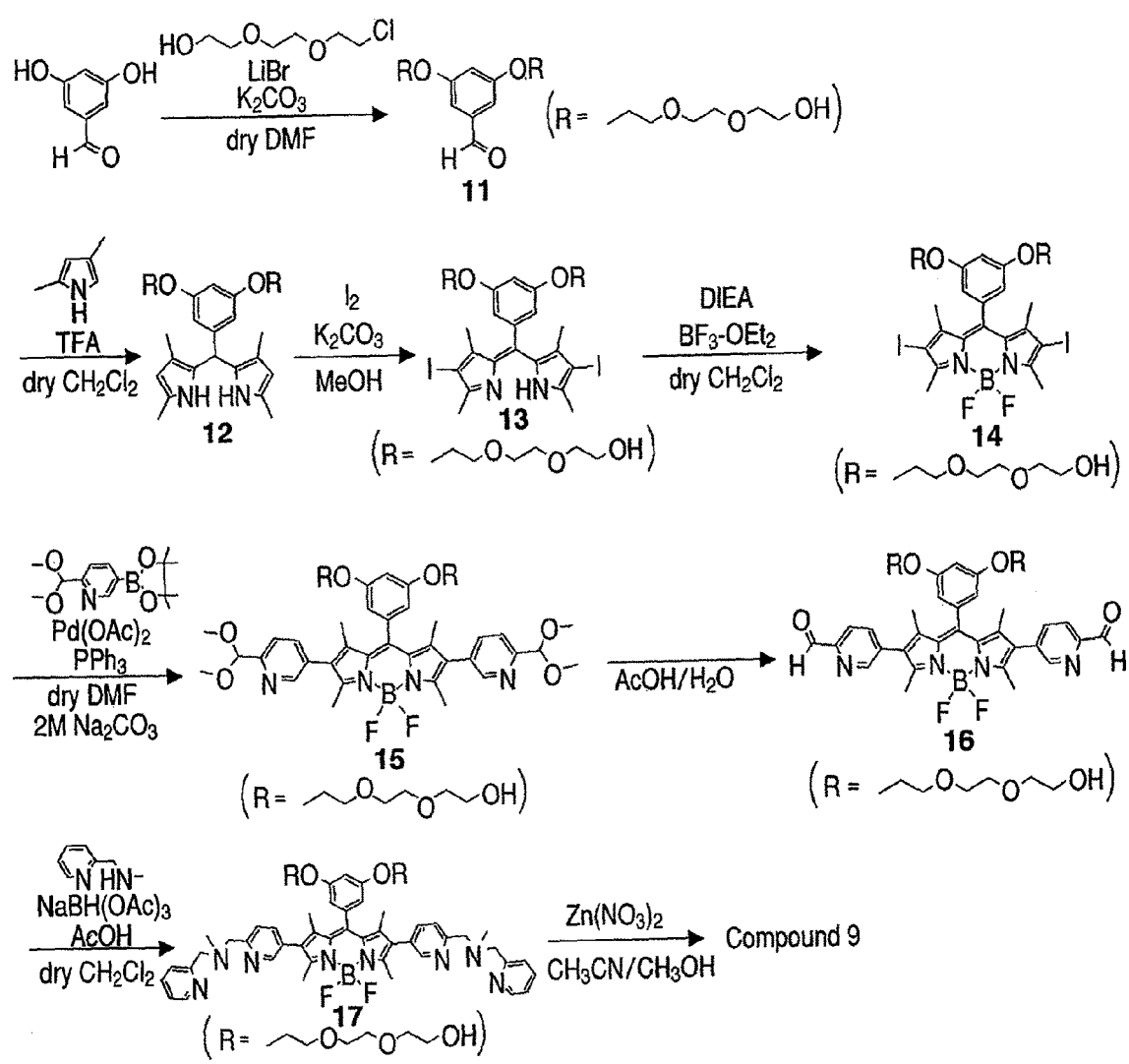
FIG. 14 illustrates a synthesis scheme of BODIPY-Zn (Dpa) (compound 9).

As another luminescent compound according to the present invention, BODIPY-Zn(Dpa) represented by the formula (12) described above (compound 9) was synthesized as follows. FIG. 14 illustrates a synthesis scheme.

Example 2(1)

Synthesis of Compound 11

1.0 g (7.24 mmol) of 3,5-dihydroxy-benzaldehyde, 2.5 g (18.1 mmol, 2.5 eq) of potassium carbonate, 628.7 mg (7.24 mmol, 1.0 eq) of lithium bromide and 35 mL of dry DMF were placed in a 100-mL three-neck recovery flask, and the mixture was stirred at 100° C. Then, a solution of triethylene glycol monochlorohydrin in dry DMF (2.31 mL (15.9 mmol, 2.2 eq)/10 mL) was added dropwise to the reaction solution, and the mixture was stirred continuously at 100° C. The reaction was followed by TLC (CHCl$_3$/MeOH=10/1), and completion of the reaction was confirmed five days later. Insoluble matters were isolated by filtration, and the filtrate was evaporated under reduced pressure. Ethyl acetate and 10% w/v aqueous potassium carbonate were added, and the mixture was extracted with ethyl acetate. Then, the organic layer was washed with 10% w/v aqueous potassium carbonate and dried with sodium sulfate, and the solvent was evaporated under reduced pressure. Purification was performed by column chromatography (silica gel, CHCl$_3$/MeOH=15/1) to obtain a light brown oily compound (yield, 2.75 g [98.0%]). Identification was performed by $^1$H-NMR.

TABLE 1

| | $^1$H-NMR (400 MHz, CDCl$_3$, 25° C., TMS); compound 11 | | | |
|---|---|---|---|---|
| δ/ppm | Splitting (J/Hz) | Integral ratio | Theoretical ratio | Assignment |
| 2.50 | d (6.0) | 1.73 | 2 H | j |
| 3.60-4.18 | m | 25.4 | 24 H | d, e, f, g, h, i |
| 6.78 | t (2.4) | 0.93 | 1 H | c |
| 7.02 | d (2.4) | 2.07 | 2 H | d |
| 9.88 | s | 1.00* | 1 H | a |

*Reference value

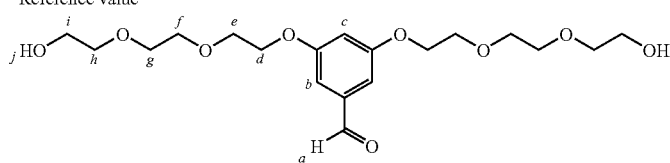

Example 2(2)

Synthesis of Compound 12

1.0 g (2.57 mmol) of compound 11, 514.3 mg (0.56 ml/2.1 eq) of 2,4-dimethylpyrrole, dry CH$_2$Cl$_2$ and one drop of TFA were placed in a 50-mL two-neck recovery flask, and the mixture was stirred at room temperature. The reaction was followed by TLC(CHCl$_3$/MeOH=10/1), and completion of the reaction was confirmed 24 h later. The reaction solution was diluted with CH$_2$Cl$_2$ and washed with aqueous saturated sodium hydrogencarbonate. The organic layer was dried with sodium sulfate, and the solvent was evaporated under reduced pressure. Purification was performed by column chromatography (silica gel, CHCl$_3$/MeOH=10/1) to obtain a brown oily compound (yield, 824.2 mg [55.7%]). Identification was performed by $^1$H-NMR.

TABLE 2

| | | | | |
|---|---|---|---|---|
| $^1$H-NMR (400 MHz, CDCl$_3$, 25° C., TMS); compound 12 | | | | |
| δ/ppm | Splitting (J/Hz) | Integral ratio | Theoretical ratio | Assignment |
| 1.83 | s | 6.00* | 6 H | a or c |
| 2.15 | s | 6.17 | 6 H | a or c |
| 3.59-4.08 | m | 24.9 | 24 H | h, I, j, k, l, m |
| 5.32 | s | 0.93 | 1 H | e |
| 5.67 | s | 1.92 | 2 H | b |
| 6.35 | d (2.4) | 2.24 | 2 H | f |
| 6.40 | t (2.0) | 0.97 | 1 H | g |
| 7.37 | s | 1.96 | 2 H | d |

*Reference value

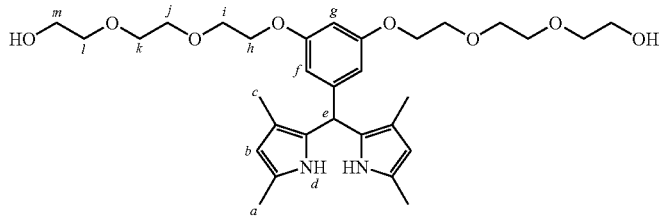

Example 2(3)

Synthesis of Compound 13

824 mg (1.43 mmol) of compound 12, 798.5 mg (3.15 mmol/2.2 eq) of iodine, 593 mg (4.29 mmol/3.0 eq) of potassium carbonate and 10 mL of methanol were placed in a 50-mL two-neck recovery flask, and the mixture was stirred at 0° C. The reaction was followed by TLC (CHCl$_3$/MeOH=10/1), and completion of the reaction was confirmed 12 h later. The mixture was extracted with chloroform and washed with aqueous saturated sodium thiosulfate. The organic layer was dried with magnesium sulfate, and the solvent was evaporated under reduced pressure to obtain a brown oily compound (yield, 886.3 mg [75.1%]). Identification was performed by $^1$H-NMR.

TABLE 3

| | | | | |
|---|---|---|---|---|
| $^1$H-NMR (400 MHz, CDCl$_3$, 25° C., TMS); compound 13 | | | | |
| δ/ppm | Splitting (J/Hz) | Integral ratio | Theoretical ratio | Assignment |
| 1.45 | s | 5.59 | 6 H | a or b |
| 2.39 | s | 6.00* | 6 H | a or b |
| 3.59-4.11 | m | 24.6 | 24 H | e, f, g, h, I, j |

TABLE 3-continued $^1$H-NMR (400 MHz, CDCl$_3$, 25° C., TMS); compound 13

| δ/ppm | Splitting (J/Hz) | Integral ratio | Theoretical ratio | Assignment |
|---|---|---|---|---|
| 6.45 | s | 1.94 | 2 H | c |
| 6.64 | s | 0.97 | 1 H | d |

*Reference value

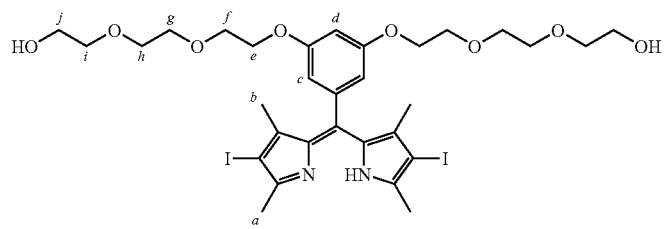

Example 2(4)

Synthesis of Compound 14

880.0 mg (1.07 mmol) of compound 13, 6.52 mL (35 eq/37.5 mmol) of DIEA and 15 mL of dry CH$_2$Cl$_2$ were placed in a 50-mL two-neck recovery flask, and the mixture was stirred at 0° C. for 10 min. Then, 5.95 mL (48 mmol) of BF$_3$—OEt$_2$ was added, and the mixture was further stirred at 0° C. The reaction was followed by TLC (CHCl$_3$/MeOH=10/1), and completion of the reaction was confirmed 2 h later. The reaction solution was washed with distilled water and 2 N aqueous NaOH, the organic layer was dried with sodium sulfate, and the solvent was evaporated under reduced pressure to obtain a black red oily compound (yield, 866.3 mg [92.8%]). Identification was performed by $^1$H-NMR.

Example 2(5)

Synthesis of Compound 15

465.4 mg (0.53 mmol) of compound 14, 739.7 mg (1.33 mmol/2.5 eq) of pyridine boronic acid, 10 mL of dry DMF, Pd(OAc)$_2$ (5% mol to S. M.) and PPh$_3$ (10% mol to S. M.) were placed in a 50-mL two-neck recovery flask deaerated by argon substitution, and the mixture was stirred at room temperature for 10 min. Then, 2 mL of 2 M aqueous Na$_2$CO$_3$ was added, and the mixture was stirred at 70° C. The reaction was followed by TLC(CHCl$_3$/MeOH=10/1, silica gel), and completion of the reaction was confirmed 2 h later. The solvent was evaporated under reduced pressure, CH$_2$Cl$_2$ was added to the residue, insoluble components were isolated by filtration, and the filtrate was evaporated under reduced pressure. Purification was performed by column chromatography (silica gel, CHCl$_3$/MeOH=10/1) to obtain a red oily compound (yield, 283.5 mg [58.0%]). Identification was performed by $^1$H-NMR.

TABLE 4

$^1$H-NMR (400 MHz, CDCl$_3$, 25° C., TMS); compound 14

| δ/ppm | Splitting (J/Hz) | Integral ratio | Theoretical ratio | Assignment |
|---|---|---|---|---|
| 1.56 | s | 11.1 (containing H$_2$O) | 6 H | a or b |
| 2.63 | s | 6.07 | 6 H | a or b |
| 3.59-4.13 | m | 25.7 | 24 H | e, f, g, h, I, j |
| 6.43 | s | 2.08 | 2 H | c |
| 6.67 | s | 1.08 | 1 H | d |

*Reference value

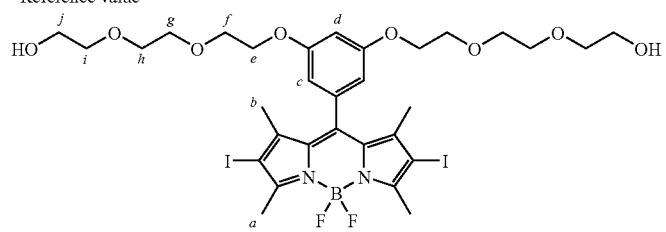

TABLE 5

<sup>1</sup>H-NMR (400 MHz, CDCl$_3$, 25° C., TMS); compound 15

| δ/ppm | Splitting (J/Hz) | Integral ratio | Theoretical ratio | Assignment |
|---|---|---|---|---|
| 1.49 | s | 5.59 | 6 H | f or g |
| 2.54 | s | 5.66 | 6 H | f or g |
| 3.46 | s | 11.65 | 12 H | a |
| 3.58-4.14 | m | 24.2 | 24 H | j, k, l, m, n, o |
| 5.40 | s | 1.87 | 2 H | b |
| 6.53 | s | 1.83 | 2 H | h |
| 6.64 | s | 1.06 | 1 H | i |
| 7.55-7.61 | m | 4.21 | 4 H | c, d |
| 8.46 | s | 2.00* | 2 H | e |

*Reference value

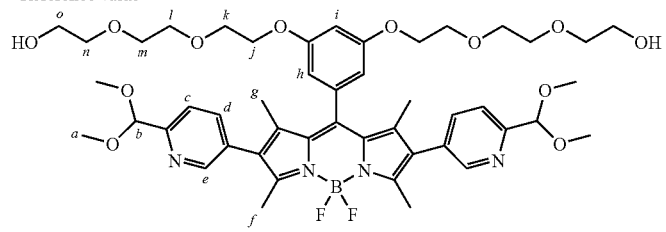

Example 2(6)

Synthesis of Compound 16

280 mg (0.30 mmol) of compound 15 and 15 mL of (3/2) were placed in a 50-mL two-neck recovery flask, and the mixture was heated to reflux. The reaction was followed by TLC(CHCl$_3$/MeOH=10/1, silica gel), and completion of the reaction was confirmed 3 h later. The reaction solution was poured on ice and neutralized with potassium carbonate. Then, the solution was extracted with chloroform, the organic layer was dried with sodium sulfate, the solvent was evaporated under reduced pressure to obtain a red oily compound (yield, 56.0 mg). Identification was performed by <sup>1</sup>H-NMR.

TABLE 6

<sup>1</sup>H-NMR (400 MHz, CDCl$_3$, 25° C., TMS); compound 16

| δ/ppm | Splitting (J/Hz) | Integral ratio | Theoretical ratio | Assignment |
|---|---|---|---|---|
| 1.52 | s | (containing H$_2$O) | 6 H | f or e |
| 2.58 | s | 6.16 | 6 H | f or e |
| 3.58-4.14 | m | 26.4 | 24 H | i, j, k, l, m, n |
| 6.54 | s | 2.40 | 2 H | g |
| 6.66 | s | 1.14 | 1 H | h |
| 7.72 | s | 2.08 | 2 H | c |
| 8.02 | d (8.0) | 2.06 | 2 H | b |
| 8.64 | d (8.0) | 2.00* | 2 H | d |
| 10.1 | s | 1.82 | 2 H | a |

*Reference value

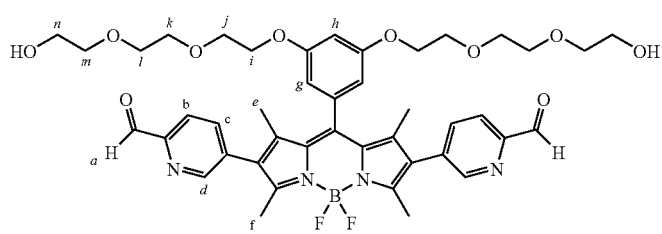

Example 2(7)

Synthesis of Compound 17

56.0 mg (0.067 mmol) of compound 16, 10 mL of dry $CH_2Cl_2$, two drops of acetic acid and 21.4 mg (2.5 eq) of aminomethylpicoline were placed in a 50-mL two-neck recovery flask, and the mixture was stirred at room temperature for 10 min. Then, 61.3 mg (3.0 eq) of was added, and the mixture was stirred at room temperature. The reaction was followed by TLC ($CHCl_3$/MeOH=10/1, containing aqueous $NH_3$, silica gel), and completion of the reaction was confirmed 24 h later. Aqueous saturated sodium hydrogencarbonate was added to the reaction solution, and the mixture was extracted with chloroform. The organic layer was dried with sodium sulfate, and the solvent was evaporated under reduced pressure. Purification was performed by column chromatography (silica gel, $CHCl_3$/MeOH=30/1, containing aqueous $NH_3$) to obtain a red oily compound (yield, 44.7 mg [63.6%]). Identification was performed by $^1$H-NMR.

TABLE 7

$^1$H-NMR (400 MHz, $CDCl_3$, 25° C., TMS); compound 17

| δ/ppm | Splitting (J/Hz) | Integral ratio | Theoretical ratio | Assignment |
|---|---|---|---|---|
| 1.48 | s | 6.20* | 6 H | k or l |
| 2.35 | s | 6.42 | 6 H | k or l |
| 2.53 | s | 6.79 | 6 H | f |
| 3.58-4.13 | m | 33.1 | 32 H | e, g, o, p, q, r, s, t |
| 6.54 | s | 2.00 | 2 H | m |
| 6.64 | s | 0.97 | 1 H | n |
| 7.16 | t (6.4) | 1.86 | 2 H | c |
| 7.47-7.57 | m | 6.26 | 6 H | d, h, i |
| 7.67 | t (8.0) | 2.18 | 2 H | b |
| 8.38 | s | 2.00 | 2 H | j |
| 8.55 | d (4.8) | 2.00* | 2 H | a |

*Reference value

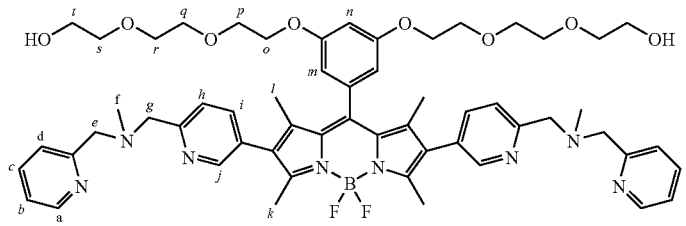

Example 2(8)

Synthesis of Compound 9

26.5 mg (0.025 mmol) of compound 17 and 10 mL of simply distilled acetonitrile/methanol were placed in a 50-mL one-neck recovery flask, and the mixture was stirred until a uniform solution was obtained. Then, 161.91 µL (1.95 eq) of 305.99 mM aqueous $Zn(NO_3)_2$ was added, and the mixture was stirred at room temperature for 1 h. The reaction solution was evaporated under reduced pressure, a small amount of distilled water was added, and the solution was lyophilized. The resulting solids were washed with ethyl acetate and hexane and dried under reduced pressure to obtain an orange color solid (yield, 30.5 mg [84.5%]). Identification was performed by $^1$H-NMR.

TABLE 8

$^1$H-NMR (400 MHz, $D_2O$ (small amount), 25° C.); compound 9

| δ/ppm | Splitting (J/Hz) | Integral ratio | Theoretical ratio | Assignment |
|---|---|---|---|---|
| 1.44 | s | 6.04 | 6 H | k or l |
| 2.31 | s | 6.46 | 6 H | k or l |
| 2.42 | s | 6.12 | 6 H | f |
| 3.48-3.79 | m | 20.7 | 20 H | p, q, r, s, t |
| 4.07-4.16 | m | 12.32 | 12 H | o, e, g |

TABLE 8-continued $^1$H-NMR (400 MHz, D$_2$O (small amount), 25° C.); compound 9

| δ/ppm | Splitting (J/Hz) | Integral ratio | Theoretical ratio | Assignment |
|---|---|---|---|---|
| 6.69-6.72 | m | 3.06 | 3 H | m, n |
| 7.48-7.57 | m | 6.51 | 2 H | c, d, i |
| 7.87 | d (7.6) | 2.23 | 6 H | h |
| 7.98 | t (8.0) | 2.44 | 2 H | b |
| 8.41 | s | 2.00* | 2 H | j |
| 8.54 | d (4.8) | 2.21 | 2 H | a |

*Reference value

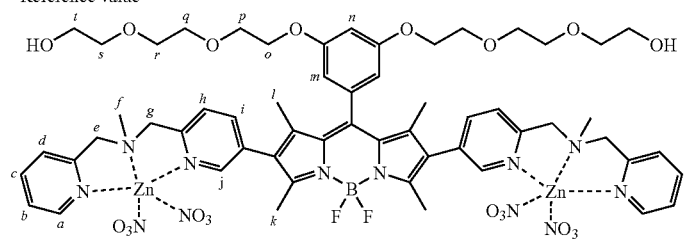

Example 2(9)

Designing of Target Multisite Phosphorylated Peptides

A partial sequence peptide of a tau protein phosphorylated at the positions of (i, i+4) among phosphorylation sites (Tau2P) was synthesized. The 231st threonine and the 235th serine were phosphorylated. Furthermore, an unphosphorylated peptide (Tau0P) and a monophosphorylated tau sequence peptide having a phosphate group at the position of i (Tau1P) were also synthesized as control peptides. The peptides were synthesized according to Example 1(13). FIG. 15 lists the synthesized phosphorylated peptides.

Example 2(10)

Analysis of Interaction Between Phosphorylated Tau Model Peptides and BODIPY-Zn(Dpa)

The phosphorylated peptide-recognizing ability of BODIPY-Zn(Dpa) compound 9 (hereinafter referred to as BODIPY-Zn(Dpa)) was evaluated by measuring fluorescence spectra. Measurement was performed under the following conditions: [BODIPY-Zn(Dpa)]=5 μM; pH 7.2; 50 mM HEPES buffer; and 25° C. The excitation wavelength was λex=530 nm. As shown in FIG. 16A, when BODIPY-Zn (Dpa) was added to Tau2P, the fluorescence intensity at 540 nm increased. When Tau2P was excessively added, this change reached saturation. The association multiplier calculated from the fluorescence changes was $2.75 \times 10^5$ M$^{-1}$. On the other hand, when Tau0P or Tau1P was added dropwise to BODIPY-Zn(Dpa), the fluorescence intensity gradually decreased with the addition of the peptide, but no major change was observed (FIG. 16B). These results are shown in Table 9. These results suggest that the increase in the fluorescence intensity in the TauP2 addition system occurred because two zinc complexes in BODIPY-Zn(Dpa) recognized two phosphate groups on the peptide. The above results revealed that BODIPY-Zn(Dpa) could detect Tau2P, here, a tau peptide with "i"th and "i+4"th amino acids being phosphorylated.

Fluorescence changes when peptide Tau$_{204-216}$3P or Tau$_{204-216}$2P used in Example 1 was added dropwise were measured to calculate the affinity (association constant). The results are shown in Table 9. While the Tau$_{204-216}$3P peptide with "i"th and "i+4"th amino acids being phosphorylated could be detected, the Tau$_{204-216}$2P peptide with "i"th and "i+6"th amino acids being phosphorylated could not be detected. The above results suggested that BODIPY-Zn(Dpa) distance-selectively recognized two phosphate groups on the peptide via a crosslinking interaction.

TABLE 9

Fluorescence changes and affinity when adding each peptide dropwise

| Peptide | SEQ ID NO: | Position of phosphate group | I/I$_0$ - 1 at saturation | Association constant/M$^{-1}$ |
|---|---|---|---|---|
| Tau 2P | 9 | i, i + 4 | 0.55 | $2.75 \times 10^5$ |
| Tau 1P | 8 | 4th from C terminus | No change | — |
| Tau 0P | 7 | — | No change | — |
| Tau$_{204-216}$ 3P | 4 | i, i + 4, i + 6 | 0.25 | $2.3 \times 10^5$ |
| Tau$_{204-216}$ 2P | 6 | i, i + 6 | No change | — |

Although the multisite phosphorylated peptide-recognizing compound with a spacer binding to a nitrogen atom in a zinc complex moiety, which has already been reported (refer to Akio Ojida et al., J. Am. Chem. Soc., (2003) 125, 10184-10185), shows a 10-fold difference in affinity, this compound interacts with both monophosphorylated peptides and diphosphorylated peptides. On the other hand, when BODIPY-Zn(Dpa) is used, the fluorescence intensity does not change in Tau1P, a monophosphorylated peptide. Since the sequence of the substrate peptide used is different from that of this example, a direct comparison cannot be made. However, it was found that, when fluorescence intensity changes were used as an indicator, selectivity to a diphosphorylated peptide improved.

Furthermore, BODIPY-Zn(Dpa) did not interact with Tau$_{204-216}$2P, a peptide phosphorylated at the "i and i+6th" positions, showing no change in the fluorescence intensity. As described above, the multisite phosphorylated peptide-recognizing compound which has already been reported (refer to Akio Ojida et al., J. Am. Chem. Soc., (2003) 125, 10184-10185), although weakly, interacts with a plurality of diphosphorylated peptides with different distances between phosphate groups. This result also revealed that, when fluorescence intensity changes were used as an indicator, BODIPY-Zn(Dpa) had an improved property of recognizing the phosphate group distance in diphosphorylated peptides.

FIG. 17 shows the Job's plot in a system with a total concentration of BODIPY-Zn(Dpa) and Tau2P of 5 µM. The graph shows that BODIPY-Zn(Dpa) and Tau2P form a complex with a stoichiometric ratio of 1:1 since the maximum value is reached in a mole ratio of 0.5.

Example 2(11)

Kinase Assay Using BODIPY-Zn(Dpa)

Figure 18:
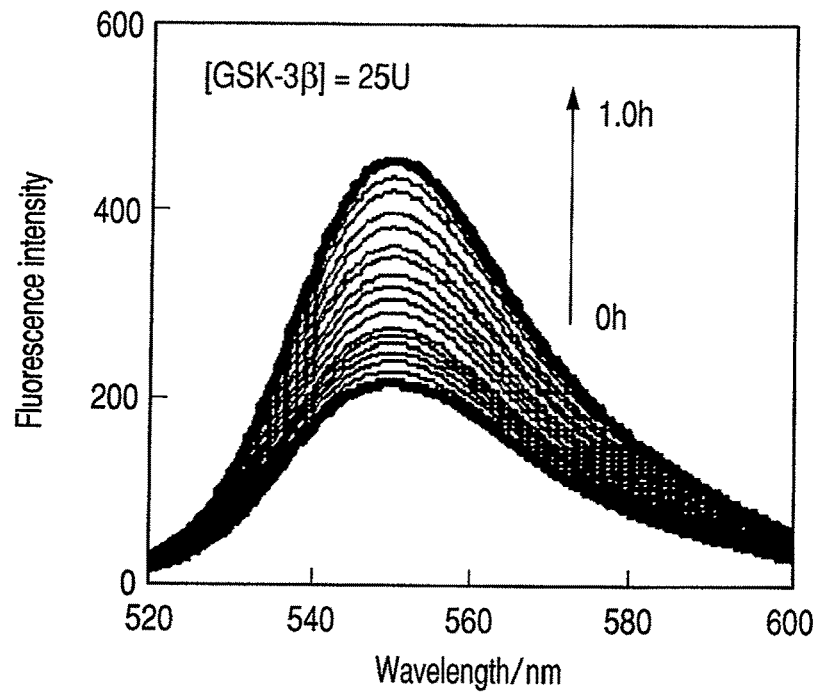
FIG. 18 illustrates changes over time in fluorescence spectra in a system with coexistence of BODIPY-Zn(Dpa), Tau P1 and GSK-3β.
Figure 19:
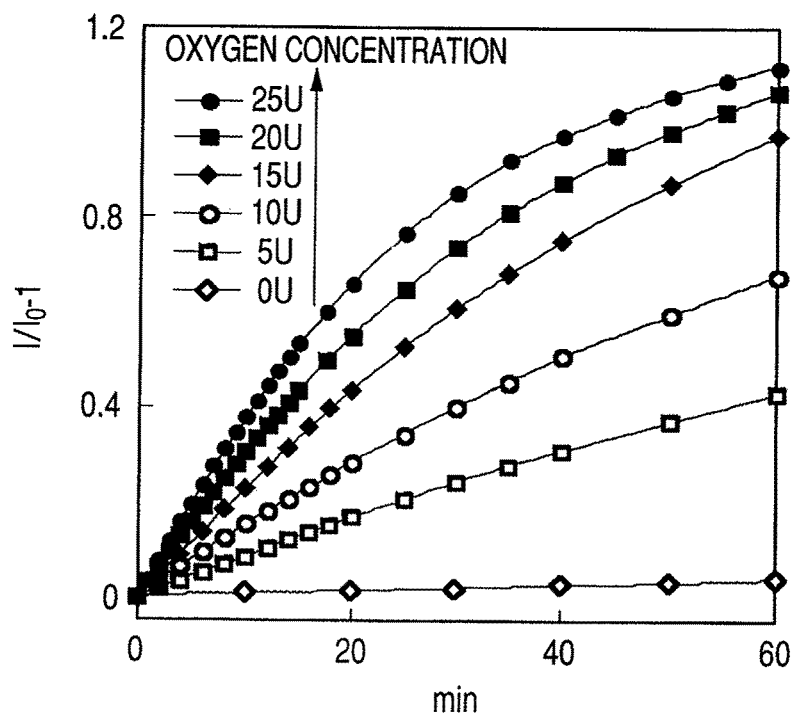
FIG. 19 illustrates kinase concentration-dependent changes in fluorescence intensity in a system with coexistence of BODIPY-Zn(Dpa), Tau P1 and GSK-3β.

A kinase assay was performed using Tau1P, a phosphorylated partial sequence peptide of a tau protein, BODIPY-Zn(Dpa) and GSK-3β, which phosphorylates the 231st threonine. The experiment conditions were as follows: 20 µM Tau1P, 20 µM BODIPY-Zn(Dpa), 100 µM ATP, 2 µg of BSA, 50 mM HEPES, 10 mM MgCl$_2$, 10 mM DTT, 2 µM EDTA; pH 7.2; 30° C.; and an excitation wavelength of 540 nm. The results are shown in FIG. 18. As shown in FIG. 18, the increase in fluorescence intensity with time was confirmed. This is a result of phosphorylation of the 231st threonine in Tau1P by GSK-3β, recognition of the phosphorylation by BODIPY-Zn(Dpa) and the resulting interaction. Furthermore, as shown in FIG. 19, the concentration-dependence of GSK-3β was observed. The results demonstrated that BODIPY-Zn(Dpa) could recognize two phosphorylation sites and detect phosphorylation by a kinase in real time.

Example 2(12)

Fluorescence Staining of Human Brain Hippocampal Tissue Using BODIPY-Zn(Dpa)

To investigate whether an excessively phosphorylated tau protein in brain tissues can be detected, a fluorescence staining experiment of hippocampal tissue sections from a human brain affected by Alzheimer (AD) and a normal brain was performed using BODIPY-Zn(Dpa). Specifically, hippocampal tissue sections from the AD-affected human brain or the normal brain were deparaffinized (xylene immersion for 5 min was repeated three times, then each section was immersed in 100%, 90%, 80% and 70% aqueous ethanol solution in stages [for 2 min each], and finally washed twice with water for 5 min), lipofuscin was removed (washed twice with PBS for 2 min, immersed in 0.25% by weight permanganate potassium/PBS for 30 min, washed twice with PBS for 2 min, immersed in 1% by weight oxalic acid and 1% by weight potassium pyrosulfate/PBS for 6 min and finally washed twice with PBS for 2 min), trypsin treatment was performed (washed twice with PBS-Tween at room temperature for 2 min and 0.05% Trypsin/PBS at 37° C. for 15 min), and finally washed twice with PBS-Tween at room temperature for 5 min, and costaining was performed using an antibody and BODIPY-Zn(Dpa). First, blocking was performed with 10% goat serum (37° C., 30 min) to remove 10% goat serum, then a primary antibody was added, and a reaction was performed at 4° C. for 17 to 19 h. Then, the sections were washed five times with PBS-Tween for 2 min (on an ice bath), a secondary antibody (AlexaFluor 633-labeled goat IgG antibody [anti-mouse IgG]) was added, and a reaction was performed at 37° C. for 1 h. The sections were washed three times with PBS-Tween for 2 min (on an ice bath), reacted with 10 µM BODIPY-Zn(Dpa) and 100 µL of 0.0001% DAPI/HBS solution at room temperature for 10 min, washed twice with 0.5 mM aqueous Zn(NO$_3$)$_2$ for 2 min (on an ice bath), and included using PermaFluor™ (Beckman Coulter). In this experiment, an anti-amyloid beta protein antibody (Aβ42; a solution attached to an Aβ staining kit [Wako]), an anti-phosphorylated tau antibody (AT8: epitope pSer202/pThr205, 1:5000 dilution), an anti-tau antibody (Tau-2: antibody recognizing both phosphorylated tau and unphosphorylated tau, 1:5000 dilution) were used as primary antibodies. The stained sections were observed under the confocal laser microscope. DAPI was observed at an excitation wavelength of 351 nm and a fluorescence wavelength of 400 to 500 nm, BODIPY-Zn(Dpa) at an excitation wavelength of 488 nm and a fluorescence wavelength of 500 to 555 nm, and AlexaFluor 633 at an excitation wavelength of 633 nm and a fluorescence wavelength of 645 to 745 nm. The staining results are shown in FIG. 20.

Figure 20:
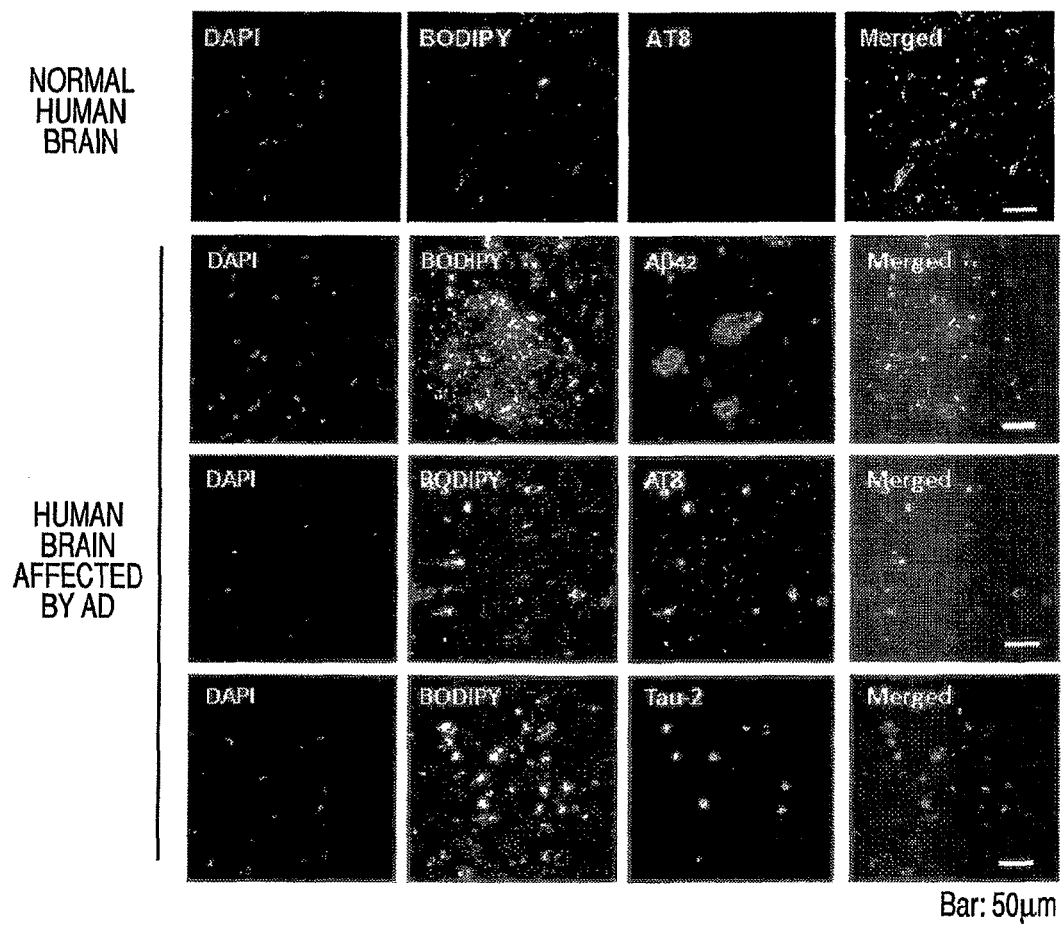
FIG. 20 illustrates fluorescence staining images of hippocampal tissue sections from the human brain affected by Alzheimer's disease (AD) and normal human brain using DAPI (cell nucleus), Aβ42 (anti-Aβ antibody), AT8 (anti-phosphorylated tau antibody), Tau-2 (anti-tau antibody) and BODIPY-Zn(Dpa). Scale bar: 50 μm.

As shown in the fluorescence staining images in FIG. 20, it was found that fluorescence of Tau-2 and BODIPY-Zn(Dpa) and fluorescence of AT8 (anti-phosphorylated tau antibody) and BODIPY-Zn(Dpa) coexisted in hippocampal tissues from the AD-affected human brain. This result suggests that BODIPY-Zn(Dpa) can bind to a phosphorylated tau protein. On the other hand, fluorescence of Aβ42 (anti-Aβ antibody) and BODIPY-Zn(Dpa) did not coexist in hippocampal tissues from the AD-affected human brain. This result suggests that BODIPY-Zn(Dpa) does not bind to an amyloid beta protein. More interestingly, since fluorescence of BODIPY-Zn(Dpa) is not observed in hippocampal tissues from the normal human brain, it was demonstrated that BODIPY-Zn(Dpa) was a compound specific to the brain affected by Alzheimer's disease. From the above results, it is understood that the BODIPY-Zn(Dpa) of the present invention captures and stains phosphorylated tau proteins with high selectivity, but does not recognize an amyloid β aggregate.

Example 2(13)

Figure 21:
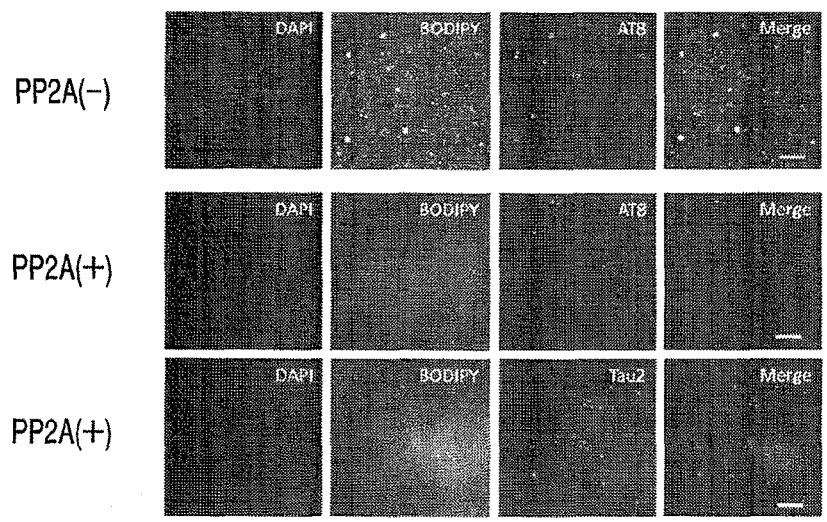
FIG. 21 illustrates a fluorescence staining image of a hippocampal tissue section from the human brain affected by Alzheimer's disease (AD) after treatment with a dephosphorylating enzyme (PP2A). For staining, DAPI (cell nucleus), BODIPY-Zn(Dpa), Tau-2 (anti-tau antibody) and AT8 (anti-phosphorylated tau antibody) were used. Scale bar: 50 μm.

Fluorescence Staining of Human Brain Hippocampal Tissues Treated with Dephosphorylating Enzyme To demonstrate that BODIPY-Zn(Dpa) recognizes phosphorylated amino acids and stains tau proteins on a tissue section, hippocampal tissue sections from the AD-affected human brain were treated with a dephosphorylating enzyme (PP2A) to examine changes in the BODIPY-Zn(Dpa) staining image. Before staining, the sections were treated with a dephosphorylating enzyme (PP2A: 0.5 units/50 µL, 37° C., 24 h), and a fluorescence staining experiment for hippocampal tissue sections was performed according to the procedure in Example 2(12). FIG. 21 illustrates the staining results. Fluorescence dots observed in the BODIPY-Zn(Dpa) staining and the AT8 staining disappeared after dephosphorylating tau proteins on tissues with PP2A. On the other hand, a clear fluorescence dot was confirmed in the Tau-2 staining image, and it was confirmed that tau protein aggregates existed in the tissue sections even after treatment with PP2A. The fluorescence dots in the BODIPY-Zn(Dpa) staining were detected depending on the phosphorylation of tau proteins. FIG. 22 shows fluorescence intensity change in BODIPY-Zn(Dpa) in hippocampal tissues after the PP2A treatment. As shown in the results of fluorescence intensity measurement, the fluorescence intensity of BODIPY-Zn(Dpa) significantly decreased after the PP2A treatment as compared with that before PP2A treatment. These results demonstrated that BODIPY-Zn(Dpa) recognized phosphorylated amino acids and stained a tau protein aggregate in hippocampal tissues from the AD-affected human brain.

Example 2(14)

Figures 24, 25:
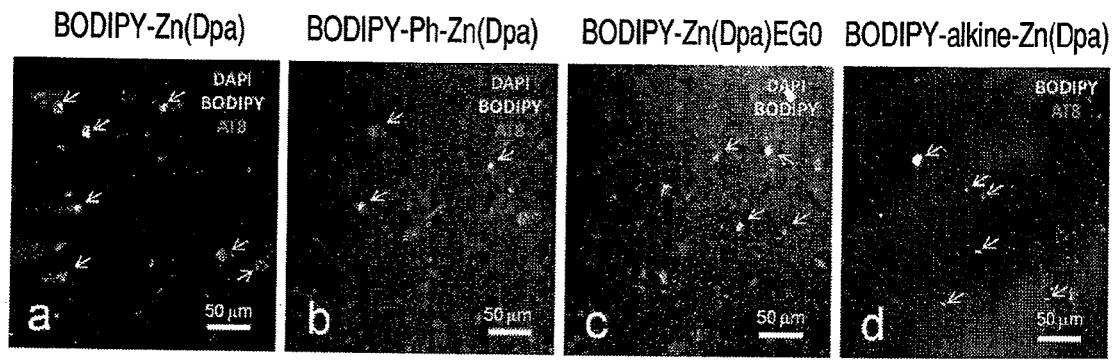
FIG. 24 illustrates fluorescence staining images of hippocampal tissue sections from the human brain affected by AD using Zn/Dpa binuclear complex compounds a to d. For staining, DAPI (cell nucleus), BODIPY-Zn(Dpa) and AT8 (anti-phosphorylated tau antibody) were used. The arrow in the figure points at the portion where fluorescence of BODIPY-Zn(Dpa) and fluorescence of the anti-phosphorylation tau antibody AT8 overlap. Scale bar: 50 μm.
FIG. 25 illustrates the maximum absorption wavelengths and partition coefficients (Pow) in the water-octanol system of Zn/Dpa binuclear complex compounds a to d.

Fluorescence Staining of AD-Affected Human Brain Hippocampal Tissues with Zn/Dpa Binuclear Complex Compounds A fluorescence staining experiment was performed for Zn/Dpa binuclear complex compounds having a similar structure (a to d in FIG. 23) using hippocampal tissues of the AD-affected human brain. The staining results of hippocampal tissues of the AD-affected human brain using these compounds are shown in FIG. 24. All the Zn/Dpa binuclear complex compounds showed fluorescence dots (pointed by arrows in the figure) which corresponded to AT8, anti-phosphorylated tau antibody, and it was suggested that these Zn/Dpa binuclear complex compounds were likely to be useful as probes for phosphorylated tau proteins.

Example 2(15)

Examination of Partition Coefficient of Zn/Dpa Binuclear Complex Compound [Water-Octanol System]

To estimate the blood-brain barrier (BBB) permeability of Zn/Dpa binuclear complex compounds, the partition coefficient (Pow) in the water-octanol system was evaluated. The BBB can be permeated through by simple diffusion when Pow is higher than 0.1. 150 µL of 1-octanol was added to 150 µL of an aqueous solution of 10 µM Zn/Dpa binuclear complex compound and vigorously mixed. The mixture was centrifuged at 1500 rpm for 2 min, and then the compound concentration in the aqueous phase was measured to determine the partition coefficient. FIG. 25 shows the maximum absorption wavelengths and the partition coefficients (Pow) of the Zn/Dpa binuclear complex compounds a to d used in Example 2(14). All the compounds showed Pow of 0.1 or higher, suggesting the possibility of BBB permeation by simple diffusion.

Example 2(16)

Measurement of BODIPY-Zn(Dpa) by 19F-NMR

BODIPY-Zn(Dpa) was measured by 19F-NMR. As a result, an F-NMR signal with a single peak at −120 ppm could be detected. This result showed that a phosphorylated tau protein or peptide could be detected by 19F-NMR or 19F-MRI using BODIPY-Zn(Dpa), the compound of the present invention.

Example 2(17)

Delivery of BODIPY-Zn(Dpa) into Brain

BODIPY-Zn(Dpa) was intravenously administered to an ICR mouse (male, 7 weeks old) to measure the delivery thereof into the brain in vivo. Specifically, BODIPY-Zn(Dpa) (400 µL of 50 µM HBS solution) was injected from the caudal vein at a dose of 1 mg/kg, and the brain was collected at 2 or 30 min after administration. The collected brain (424 to 488 mg) was homogenized in 3 mL of an HBS solution using a spatula and homogenized by ultrasonic irradiation. BODIPY-Zn(Dpa) contained in the brain was quantified by reverse-phase HPLC to obtain the content of BODIPY-Zn(Dpa) in the brain based on the dose (% ID/g: % injected dose per gram of the brain). Fluorescence from the compound (excitation, 520 nm; fluorescence, 545 nm) was utilized for detection by HPLC.

Figure 26A:
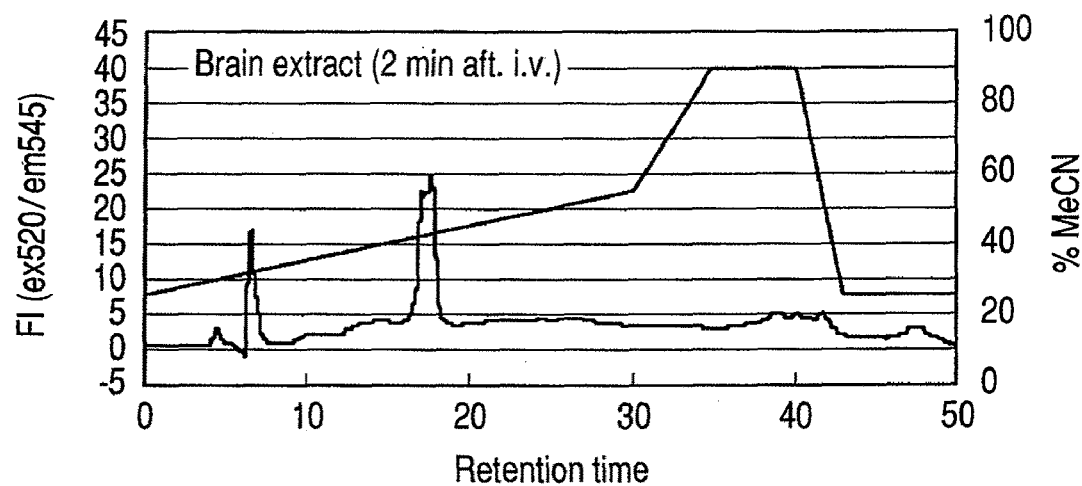
FIGS. 26A and 26B illustrate the results for evaluation of the brain uptake of BODIPY-Zn(Dpa).
Figure 26B:
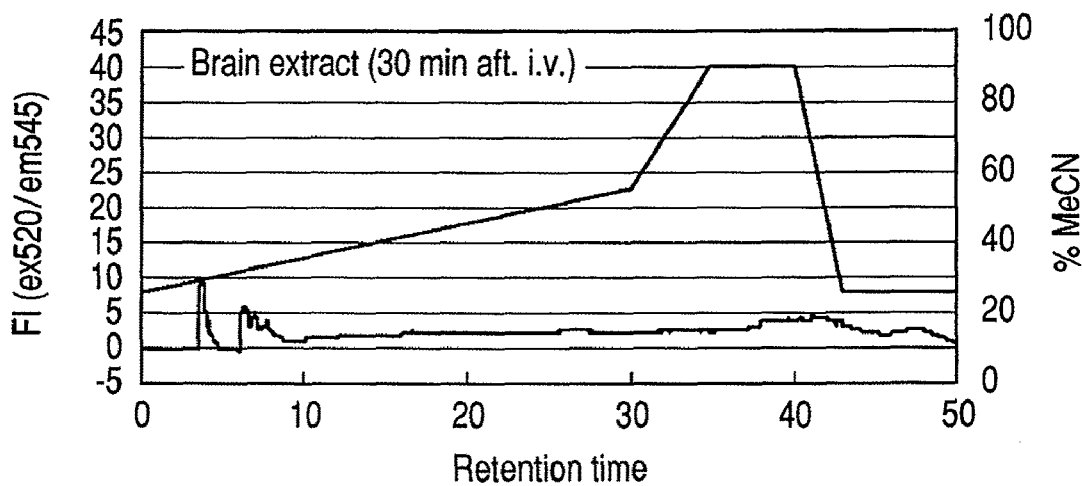

FIG. 26 shows an HPLC chart of the homogenate solution of the brain from the mouse to which BODIPY-Zn(Dpa), the compound of the present invention, was intravenously administered. At 2 min after administration, 0.5% of the dose of BODIPY-Zn(Dpa) per gram of the mouse brain (0.496% ID/g, 99.3 pmol/g brain) was found to exist in the brain. At 30 min after administration, 0.02% of the dose per gram of the mouse brain (0.020% ID/g, 3.96 pmol/g brain) was found to exist in the brain. In SPECT imaging or PET imaging, the brain delivery required for a central nervous system contrast medium is 0.5% ID/g or higher (Japanese Patent Application Laid-Open No. 2004-67659). As shown in the above results, the compound of the present invention can be used as a contrast medium having practical brain delivery for imaging phosphorylated tau proteins.

Example 2(18)

Testing of BODIPY-Zn(Dpa) Binding to Phosphorylated Tau Aggregate Prepared In Vitro Tau proteins (8 µM) expressed by *Escherichia coli* and heparin (1.6 µM) were incubated at 37° C. for 20 days to prepare a tau aggregate. A phosphorylated tau aggregate was similarly prepared using tau proteins phosphorylated with GSK-3β in vitro. The results of Pro-Q diamond staining after performing SDS-PAGE confirmed that the in-vitro phosphorylation was performed with a phosphorylation degree of 6 mol P/mol Tau.

10 µM BODIPY-Zn(Dpa) or 10 µM thioflavine T (may be referred to as ThT) were added to the prepared tau aggregate or phosphorylated tau aggregate. After the addition, the mixture was washed twice with 0.5 mM $Zn(NO_3)_2$, and a suspension (0.5 µL) of the stained phosphorylated tau aggregate was air-dried on a cover glass and observed under a confocal laser scanning microscope (OLYMPUS FV-1000, Obj. lens 100×). Thioflavine T was observed at an excitation wavelength of 458 nm and a fluorescence wavelength of 470 to 490 nm. BODIPY-Zn(Dpa) was observed at an excitation wavelength of 488 nm and a fluorescence wavelength of 560 to 580 nm.

Figure 27:
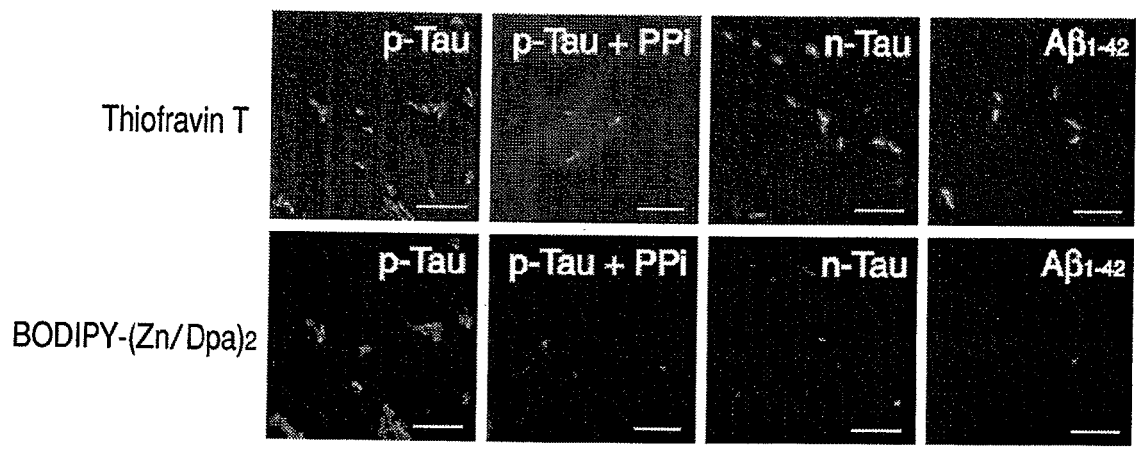
FIG. 27 illustrates simultaneous fluorescence staining images of phosphorylated Tau aggregate by thioflavine T (upper) and BODIPY-Zn(Dpa) (lower). Scale bar=10 μm. (p-Tau) indicates phosphorylated Tau aggretage, (p-Tau+PPi) indicates phosphorylated Tau aggregate under existence of pyrophosphoric acid. (n-Tau) indicates nonphosphorylated Tau aggretage. (Aβ$_{1-42}$) indicates amyloid β aggregate.

FIG. 27 shows simultaneous fluorescence staining images of the phosphorylated tau aggregate (p-Tau) using thioflavine T (ThT: upper column) and BODIPY-Zn(Dpa) (lower column). It was confirmed by the fluorescence images in FIG. 27 (p-Tau) that fluorescence of ThT and that of BODIPY-Zn (Dpa) overlapped. This result showed that fluorescence of BODIPY-Zn(Dpa) was from the p-Tau aggregate, and BODIPY-Zn(Dpa) could bind to and stain the p-Tau aggregate. In the presence of pyrophosphoric acid (PPi), ThT stained the aggregate, but BODIPY-Zn(Dpa) did not stain the aggregate as shown in the fluorescence staining image in FIG. 27 (p-Tau+PPi). These results suggest that an interaction between BODIPY-Zn(Dpa) and p-Tau is inhibited by PPi, and it was found that BODIPY-Zn(Dpa) bound to the p-Tau aggregate by recognizing phosphoric acid. FIG. 27 (n-Tau) shows that the aggregate is observed by fluorescence of ThT, but the aggregate is not observed by fluorescence of BODIPY-Zn(Dpa). These results suggest that a nonphosphorylated Tau aggregate (n-Tau) is not stained by BODIPY-Zn (Dpa) if a phosphate group does not exist on the aggregate, and it was confirmed that BODIPY-Zn(Dpa) bound to the p-Tau aggregate by recognizing a phosphate group. FIG. 27 ($Aβ_{1-42}$) shows that the amyloid β aggregate was observed by fluorescence of ThT, but the aggregate was not observed by fluorescence of BODIPY-Zn(Dpa). These results suggest that BODIPY-Zn(Dpa) does not stain an amyloid β aggregate but stains a p-Tau aggregate, showing binding selectivity to p-Tau aggregate. The above results confirmed high binding selectivity of BODIPY-Zn(Dpa) of the present invention to a phosphorylated tau aggregate.

Example 2(19)

Evaluation of Interaction Between Phosphorylated Tau Aggregate and BODIPY-Zn(Dpa) 1 (Fluorescence Titration)

The ranges of concentrations at which a phosphorylated tau aggregate, a tau aggregate, and an amyloid β aggregate interact with BODIPY-Zn(Dpa) were examined by titration. Titration was performed in the range of tau concentrations of 0 to 320 nM (0 to 14 μg/mL) against 100 nM of BODIPY-Zn(Dpa). Using a solvent obtained by adding 10% DMSO and 10 μM $Zn(NO_3)_2$ to HBS (10 mM HEPES (pH 7.4), 150 mM NaCl), the solution was incubated at 37° C. for 60 min, and fluorescence was measured (excitation wavelength, 490 nm; fluorescence wavelength, 545 nm).

Figure 28:
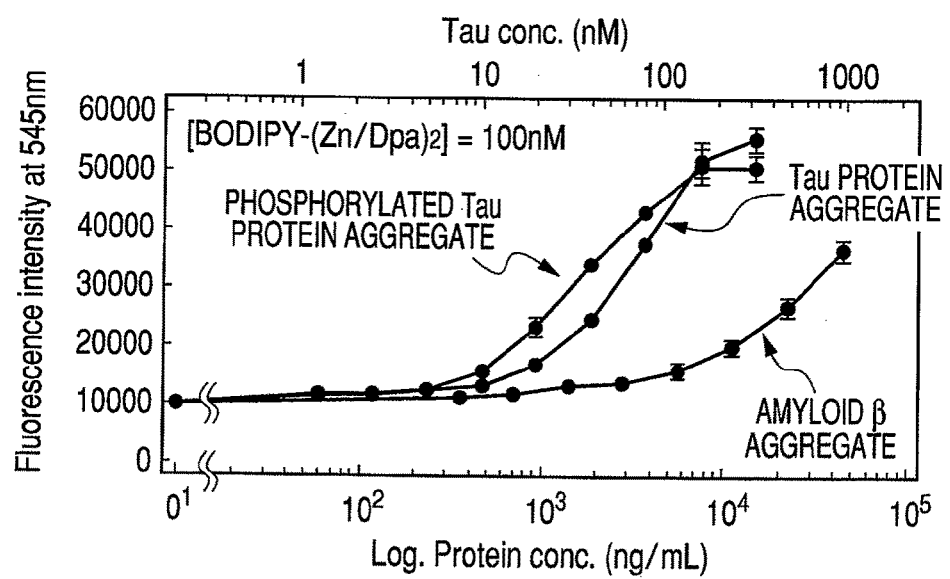
FIG. 28 illustrates the titration curves of the phosphorylated tau aggregate, the tau aggregate, and the amyloid β aggregate against BODIPY-Zn(Dpa).

FIG. 28 shows the titration curves of the phosphorylated tau aggregate, the tau aggregate, and the amyloid β aggregate against BODIPY-Zn(Dpa). It was confirmed that the tau aggregate interacted with BODIPY-Zn(Dpa) in the range of nM. It was found that a fluorescence change occurred in the phosphorylated tau aggregate at the lowest concentration.

Example 2(20)

Evaluation of Interaction Between Phosphorylated Tau Aggregate and BODIPY-Zn(Dpa) 2 (Fluorescence Titration)

BODIPY-Zn(Dpa) was titrated against a phosphorylated tau aggregate, a tau aggregate, and an amyloid β aggregate to obtain $EC_{50}$ (a probe concentration at which a half value of the maximum change ($\Delta F_{max}$) in fluorescence intensity is observed). BODIPY-Zn(Dpa) was titrated against an aggregate at a predetermined concentration (1 μg/mL), and changes in fluorescence intensity at each concentration ($\Delta F$) were plotted. Using a solvent obtained by adding 10% DMSO and 100 μM $Zn(NO_3)_2$ to HBS (10 mM HEPES (pH 7.4), 150 mM NaCl), the solution was incubated at 37° C. for 30 min, and fluorescence was measured (excitation wavelength, 490 nm; fluorescence wavelength, 545 nm).

Figure 29:
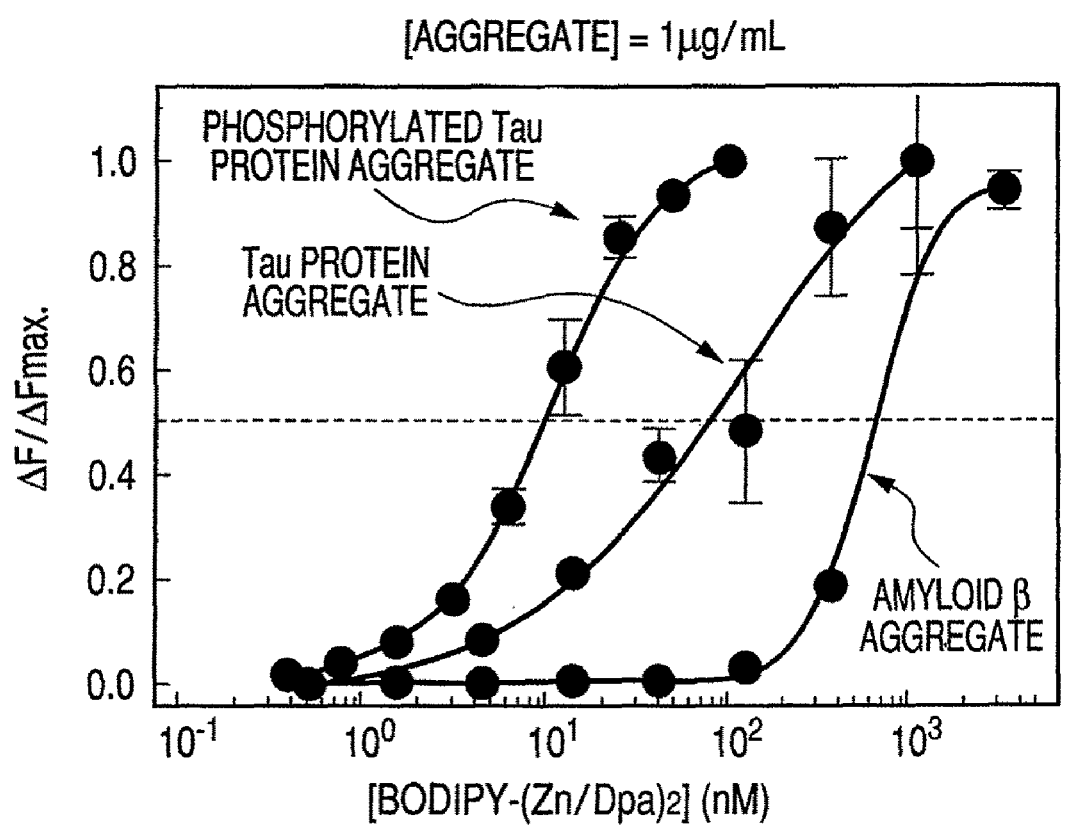
FIG. 29 illustrates the titration curves of BODIPY-Zn(Dpa) against the phosphorylated tau aggregate, tau aggregate, and the amyloid β aggregate.

FIG. 29 shows titration curves of BODIPY-Zn(Dpa) against the phosphorylated tau aggregate, the tau aggregate, and the amyloid β aggregate. The $EC_{50}$ values against the phosphorylated tau aggregate, the tau aggregate, and the amyloid β aggregate were 9.1, 80, and 650 nM, respectively. The affinity ($EC_{50}$) of BODIPY-Zn(Dpa) for the phosphorylated tau aggregate was 9 times higher than for the tau aggregate and 70 times higher than for the amyloid β aggregate. That is, high binding selectivity to the phosphorylated tau aggregate was confirmed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-048281, filed Feb. 28, 2008 which is hereby incorporated by reference herein in its entirety.

---

What is claimed is:

1. A compound having a structure comprising two 2,2'-dipicolylamine (Dpa) moieties and a spacer X, represented by formula (1):

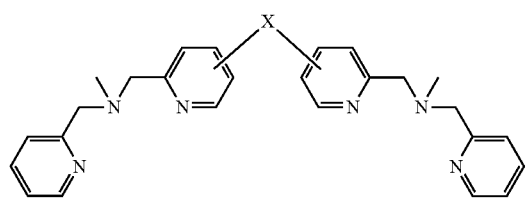
(1)

wherein a hydrogen atom in the Dpa may be replaced by an atom or an atom group other than hydrogen, and wherein the spacer X is selected from the group consisting of the following formulas (2), (3), (4) and (5):

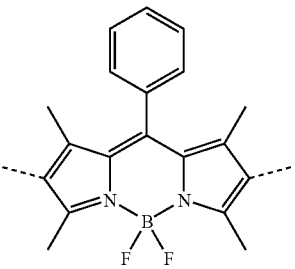
(2)

wherein the dotted line represents a site at which the spacer X binds to a pyridine ring in the Dpa, and a hydrogen atom in the phenyl group may be replaced by an atom or an atom group other than hydrogen;

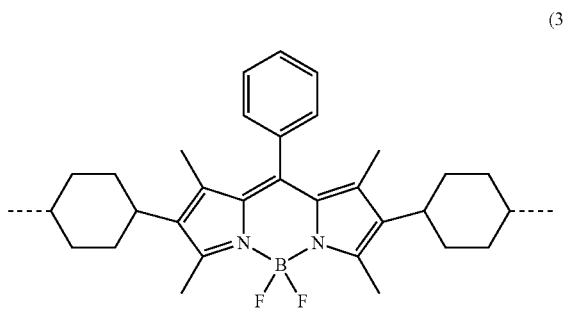
(3)

wherein the dotted line represents a site at which the spacer X binds to a pyridine ring in the Dpa, and a hydrogen atom in the phenyl group and/or a hydrogen atom in the phenylene group may be replaced by an atom or an atom group other than hydrogen;

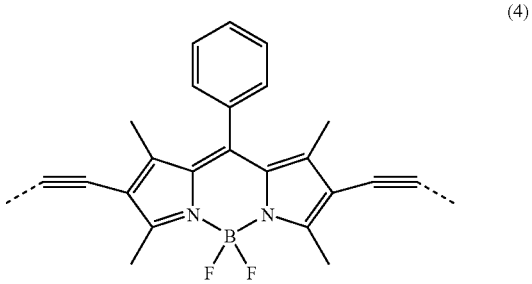
(4)

wherein the dotted line represents a site at which the spacer X binds to a pyridine ring in the Dpa, and a hydrogen atom in the phenyl group may be replaced by an atom or an atom group other than hydrogen; and

(5)

wherein the dotted line represents a site at which the spacer X binds to a pyridine ring in the Dpa.

2. The compound according to claim 1, wherein a structure in which each dipicolylamine (Dpa) forms a complex together with a metal M, represented by formula (6):

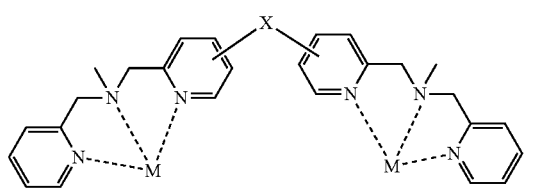
(6)

wherein X represents a spacer molecule, and a hydrogen atom in the Dpa may be replaced by an atom or an atom group other than hydrogen.

3. The compound according to claim 1, wherein a structure in which each dipicolylamine (Dpa) forms a complex together with zinc, represented by formula (7):

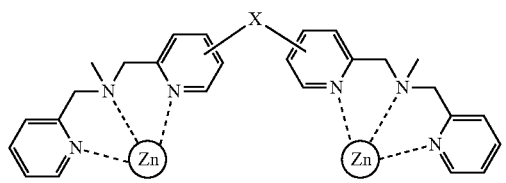

(7)

wherein X represents a spacer molecule, and a hydrogen atom in the Dpa may be replaced by an atom or an atom group other than hydrogen.

4. The compound according to claim 1, which has, in addition to the structure represented by the formula (1), any of an ethylene glycol chain, a luminescent substance, a chromogenic substance, a nuclear magnetic resonance active nuclide, a paramagnetic substance, a magnetic particle, a γ ray emitting nuclide and a positron-emitting nuclide.

5. A method for optically detecting a phosphorylated peptide or protein using the compound according to claim 2, wherein, along with contact between the phosphorylated peptide or protein and the compound, the compound is crosslinked to a phosphate group in the peptide or protein, resulting in induction of a change in a luminescence signal of the compound, and this change is measured.

6. A compound represented by one selected from the following formulas (12) to (16).

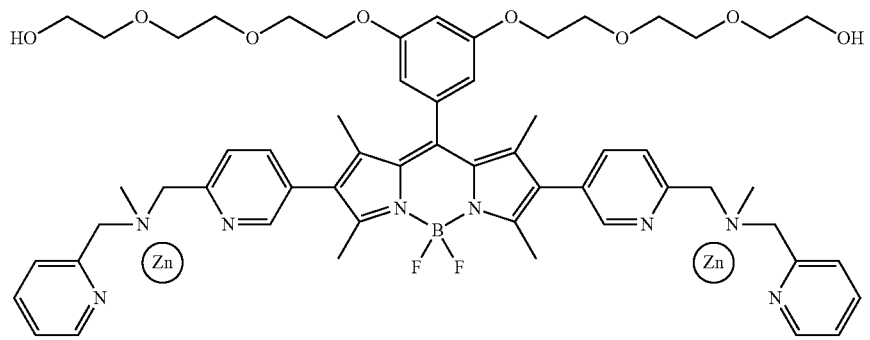

(12)

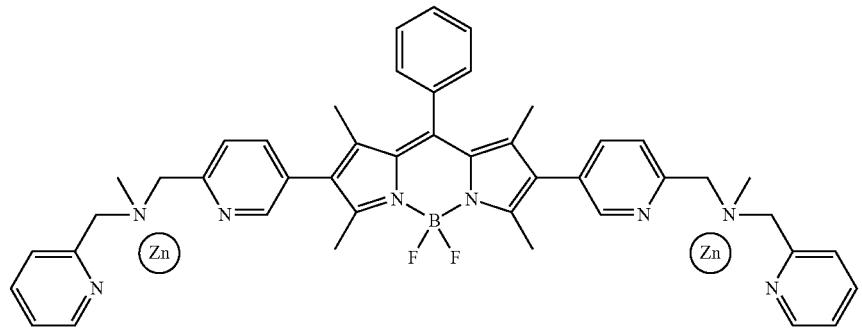

(13)

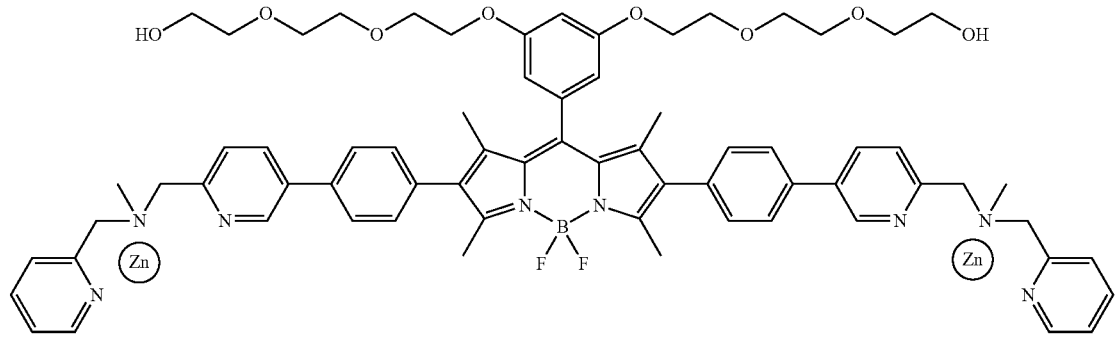

(14)

-continued
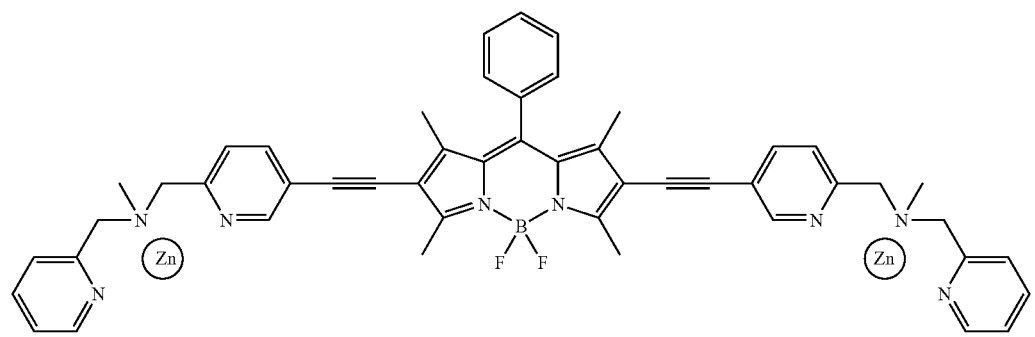
(15)
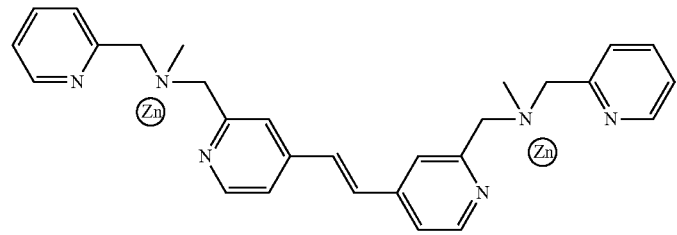
(16)
* * * * *